United States Patent
Podsakoff et al.

(10) Patent No.: US 6,582,692 B1
(45) Date of Patent: Jun. 24, 2003

(54) RECOMBINANT ADENO-ASSOCIATED VIRUS VIRIONS FOR THE TREATMENT OF LYSOSOMAL DISORDERS

(75) Inventors: Gregory Podsakoff, Fullerton, CA (US); Gordon Watson, El Sobrante, CA (US)

(73) Assignees: Avigen, Inc., Alameda, CA (US); Children's Hospital Medical Center of Northern California, Oakland, CA (US)

(*) Notice: Subject to any disclaimer, the term of this patent is extended or adjusted under 35 U.S.C. 154(b) by 0 days.

(21) Appl. No.: 09/715,858

(22) Filed: Nov. 17, 2000

Related U.S. Application Data

(60) Provisional application No. 60/166,097, filed on Nov. 17, 1999, and provisional application No. 60/215,430, filed on Jun. 30, 2000.

(51) Int. Cl.$^7$ .......................... A01N 63/00; A61K 48/00
(52) U.S. Cl. ................... 424/93.2; 435/320.1; 435/455; 514/44
(58) Field of Search .................... 514/44; 424/93.2, 424/94.61; 435/320.1, 457, 455

(56) References Cited

U.S. PATENT DOCUMENTS

| | | | | |
|---|---|---|---|---|
| 5,139,941 A | * | 8/1992 | Muzyczka et al. | 435/172.3 |
| 5,252,479 A | * | 10/1993 | Srivastava | 435/235.1 |
| 5,622,856 A | | 4/1997 | Natsoulis | 435/325 |
| 5,753,500 A | * | 5/1998 | Shenk et al. | 435/320.1 |
| 5,846,528 A | | 12/1998 | Podsakoff et al. | 424/93.2 |
| 5,858,351 A | | 1/1999 | Podsakoff et al. | 424/93.2 |
| 5,945,335 A | | 8/1999 | Colosi | 435/369 |
| 5,952,221 A | | 9/1999 | Kurtzman et al. | 435/320.1 |
| 5,962,313 A | | 10/1999 | Podsakoff et al. | 435/320.1 |
| 6,001,650 A | | 12/1999 | Colosi | 435/369 |
| 6,004,797 A | | 12/1999 | Colosi | 435/235.1 |
| 6,027,931 A | | 2/2000 | Natsoulis | 435/235.1 |
| 6,066,626 A | * | 5/2000 | Yew et al. | 514/44 |
| 6,221,349 B1 | * | 4/2001 | Couto et al. | 424/93.2 |
| 6,328,958 B1 | * | 12/2001 | Amalfitano et al. | 424/93.2 |
| 6,335,011 B1 | * | 1/2002 | Podsakoff et al. | 424/93.2 |

FOREIGN PATENT DOCUMENTS

| | | |
|---|---|---|
| WO | WO 98/24479 | 6/1998 |
| WO | WO 98/24924 | 6/1998 |

OTHER PUBLICATIONS

JE Murphy et al., Proc.Natl.Acad.Sci.USA, "Long–term correction of obesity and diabetes in genetically obese mice by a single intramuscular injection of recombinant adeno–associated virus encoding mouse leptin," Dec. 1997, vol. 94, pp. 13921–13926.*

Budker et al., The efficient expression expression of intra-vascularly delivered DNA in rat muscle, 1998, Gene Therapy, vol. 5, pp. 27–276.*

Anderson, Human gene therapy, 1998, Nature, vol. 392, pp. 25–30.*

Verma et al., Gene therapy–promises, problems and prospects, 1997, Nature, vol. 389, pp. 239–242.*

Suzuki et al., Mouse models of human lysosomal diseases, 1998, Brain Pathology, vol. 8, pp. 195–215.*

Jung, et al., "Adeno–associated viral vector–mediated gene transfer results in long–term enzymatic and fuctional correction in multiple organs of Fabry mice," *Proc. Natl. Acad. Sci. USA* 98:2676–2681 (2001).

Qasba, et al., "Long Term Enzymatic and Functional Correction in Multiple Organs of Fabry Mice Using Adeno–Associated Viral Gene Transfer," *Amer. Soc. Gene. Ther.*, Abstract 829 (2001).

Shull, et al., "Intramuscular Administration of Adeno–Associated Virus Vector Leads to α–L–Iduronidase Production in Canine Mucopolysaccharidosis I," *Gene. Ther. Abstr.*, Sep. 25–29, p. 285 (1996).

Takahashi, et al.,"Muscle mediated gene therapy of Fabry disease," *Amer. Soc. Gene. Ther.*, Abstract 640 (2001).

Wang, et al., "Sustained correction of bleeding disorder in hemophilia B mice by gene therapy," *PNAS* 96(7):3906–3910 (1999).

Ziegler, et al., "Correction of Enzymatic and Lysosomal Storage Defects in Fabry Mice by Adenovirus–Mediated Gene Transfer," *Human Gene Therapy* 10:1667–1682 (1999).

Ziegler, et al., "Gene Therapy of Fabry Disease using Recombinant Adeno–Associated Virus Vectors," *Amer. Soc. Gene. Ther.*, Abstract 655 (2001).

Sferra, et al., "Use of a Recombinant Adeno–Associated Virus to Correct Hepatic Lysosomal Storage in Mucopolysacchridosis Type VI Mice," *Gastroenterology* 116(4):A577 (1999).

Sferra et al., "Recombinant Adeno–Associated Virus–Mediated Correction of Lysosomal Storage Within the Central Nervous System of the Adult Mucopolysaccharidosis Type VII Mouse," *Human Gene Therapy* 11(4):507–519 (2000).

Sugiyama et al., "Defective Adenoassociated Viral–Mediated Transfection of Insulin Gene by Direct Injection into Liver Parenchyma Decreases Blood Glucose of Diabetic Mice," *Hormone and Metabolic Research* 29(12):599–603 (1997).

(List continued on next page.)

*Primary Examiner*—Scott D. Priebe
*Assistant Examiner*—Brian Whiteman
(74) *Attorney, Agent, or Firm*—Roberta L. Robins; Cooley Godward LLP

(57) ABSTRACT

AAV expression vectors and recombinant virions produced using these vectors, which include genes coding for enzymes defective or missing in lysosomal storage disorders, are described. These recombinant AAV virions are useful in the treatment of a variety of lysosomal storage disorders and the methods described herein provide for long-term, sustained expression of the defective or missing enzyme.

8 Claims, 12 Drawing Sheets

OTHER PUBLICATIONS

Naffakh et al., "Gene Therapy for Lysosomal Disorders," *Nov Rev Fr Hematol* 36(Suppl.I):S11–S16 (1994).

Barranger et al., "Gene Transfer Approaches to Lysosomal Storage Disorders," *Neurochemical Research* 24(4):601–615 (1999).

Daly et al., "Neonatal Gene Transfer Leads to Widespread Correction of Pathology in a Murine Model of Lysosomal Storage Disease," *Proc. Natl. Acad. Sci. U.S.A.* 96:2296–2300 (1999).

Daly et al., "Neonatal Intramuscular Injection with Recombinant Adeno–Associated Virus Results in Prolonged β–Glucuronidase Expression in Situ and Correction of Liver Pathology in Mucopolysaccharidosis Type II Mice," *Human Gene Therapy* 10:85–94 (1999).

Elliger et al., "Elimination of Lysosomal Storage in Brains of MPS VII Mice Treated by Intrathecal Administration of an Adeno–Associated Virus Vector," *Gene Therapy* 6:1175–1178 (1999).

Fisher et al., "Recombinant Adeno–Associated Virus for Muscle Directed Gene Therapy," *Nature Med.* 3:306–312 (1997).

Flotte et al., "Stable in vivo Expression of the Cystic Fibrosis Transmembrane Conductance Regulator With an Adeno–Associated Virus Vector,"*Proc. Natl. Acad. Sci. U.S.A.* 90:10613–10617 (1993).

Guidotti et al., "Adenoviral Gene Therapy of the Tay–Sachs Disease in Hexosaminidase A–Deficient Knock–Out Mice," *Human Molecular Genetics* 8(5):831–838 (1999).

Hartung et al., "Enzymatic Correction and Cross–Correction of Mucopolysaccharidosis Type I Fibroblasts by Adeno–Associated Virus–Mediated Transduction of the α–L–Iduronidase Gene," *Human Gene Therapy* 10:2163–2172 (1999).

Herzog et al., "Stable Gene Transfer and Expression of Human Blood Coagulation Factor IX After Intramuscular Injection of Recombinant Adeno–Associated Virus," *Proc. Natl. Acad. Sci. U.S.A.* 94:5804–5809 (1997).

Jensen et al., "Retrovirus–Mediated Gene Transfer of Ornithine–δ–Aminotransferase into Keratinocytes from Gyrate Atrophy Patients," *Human Gene Therapy* 8:2125–2132 (1997).

Kaplitt et al., "Long–term Gene Expression and Phenotypic Correction Using Adeno–Associated Virus Vectors in the Mammalian Brain," *Nat. Genet.* 8:148–154 (1994).

Kessler et al., "Gene Delivery to Skeletal Muscle Results in Sustained Expression and Systemic Delivery of a Therapeutic Protein," *Proc Natl Acad Sci* 93:14082–14087 (1996).

Lacorazza et al., "Correction of Ornithine–δ–Aminotransferase Deficiency in a Chinese Hamster Ovary Cell Line Mediated by Retrovirus Gene Transfer," *Gene Therapy* 2:22–28 (1995).

Li et al., "Phenotype Correction in Retinal Pigment Epithelium in Murine Mucopolysaccharidosis VII by Adenovirus–Mediated Gene Transfer," *PNAS* 92:7700–7704 (1995).

Monahan et al., "Direct Intramuscular Injection With Recombinant AAV Vectors Results in Sustained Expression in a Dog Model of Hemophilia," *Gene Therapy* 5:40–49 (1998).

O'Connor et al., Enzyme Replacement Therapy for Murine Mucopolysaccharidosis Type VII Leads to Improvements in Behavior and Auditory Function, *J. Clin. Invest.* 101:1394–1400 (1998).

Ohashi et al., "Adenovirus–Mediated Gene Transfer and Expression of Human β–Glucuronidase Gene in the Liver, Spleen, and Central Nervous System in Mucopolysaccharidosis Type VII," *Proc. Natl. Acad. Sci USA* 94:1287–1292 (1997).

Peel et al., "Efficient Transduction of Green Fluorescent Protein in Spinal Cord Neurons Using Adeno–associated Virus Vectors Containing Cell Type–specific Promoters," *Gene Therapy* 4:16–24 (1997).

Rivero et al., "Retrovirus–Mediated Gene Transfer and Expression of Human Ornithine δ–Aminotransferase into Embryonic Fibroblast," *Human Gene Therapy* 5:701–707 (1994).

Stein et al., "Systemic and Central Nervous System Correction of Lysosomal Storage in Mucopolysaccharidosis Type VII Mice," *Journal of Virology* 73:(4):3424–3429 (1999).

Takenaka et al., "Circulating α–Galactosidase A Derived From Transduced Bone Marrow Cells: Relevance for Corrective Gene Transfer for Fabry Disease," *Human Gene Therapy* 10:1931–1939 (1999).

Taylor et al., "Decreased Lysosomal Storage in the Adult MPS VII Mouse Brain in the Vicinity of Grafts of Retroviral Vector–corrected Fibroblasts Secreting High Levels of β–Glucuronidase," *Nature Med.* 3:771–774 (1997).

Vogler et al., "Enzyme Replacement With Recombinant β–Glucuronidase in the Newborn Mucopolysaccharidosis Type VII Mouse," *Pediatric Research* 34:837–840 (1993).

Watson et al., "Treatment of Lysosomal Storage Disease in MPS VII Mice Using a Recombinant Adeno–Associated Virus," *Gene Therapy* 5:1642–1649 (1998).

Xiao et al., "Efficient Long–Term Gene Transfer into Muscle Tissue of immunocompetent Mice by Adeno–Associated Virus Vector," *J. Virol.* 70:8089–8108 (1996).

* cited by examiner

Glucocerebrosidase Vectors

AAV-CMV-hGC

AAV-ApoEHCR/hAAT-hGC

SEQUENCE LISTING

```
<160> NUMBER OF SEQ ID NOS:  16

<210> SEQ ID NO 1
<211> LENGTH: 1956
<212> TYPE: DNA
<213> ORGANISM: Homo sapiens
<220> FEATURE:
<221> NAME/KEY: CDS
<222> LOCATION: (1)..(1956)

<400> SEQUENCE: 1 atg gcc cgg ggg tcg gcg gtt gcc tgg gcg gcg ctc ggg ccg ttg ttg        48
Met Ala Arg Gly Ser Ala Val Ala Trp Ala Ala Leu Gly Pro Leu Leu
 1               5                  10                  15
```

| | | |
|---|---|---|
| tgg ggc tgc gcg ctg ggg ctg cag ggc ggg atg ctg tac ccc cag gag<br>Trp Gly Cys Ala Leu Gly Leu Gln Gly Gly Met Leu Tyr Pro Gln Glu<br>                 20                       25               30 | 96 | |
| agc ccg tcg cgg gag tgc aag gag ctg gac ggc ctc tgg agc ttc cgc<br>Ser Pro Ser Arg Glu Cys Lys Glu Leu Asp Gly Leu Trp Ser Phe Arg<br>            35                   40                   45 | 144 | |
| gcc gac ttc tct gac aac cga cgc cgg ggc ttc gag gag cag tgg tac<br>Ala Asp Phe Ser Asp Asn Arg Arg Arg Gly Phe Glu Glu Gln Trp Tyr<br>50                       55                   60 | 192 | |
| cgg cgg ccg ctg tgg gag tca ggc ccc acc gtg gac atg cca gtt ccc<br>Arg Arg Pro Leu Trp Glu Ser Gly Pro Thr Val Asp Met Pro Val Pro<br>65                       70                   75                   80 | 240 | |
| tcc agc ttc aat gac atc agc cag gac tgg cgt ctg cgg cat ttt gtc<br>Ser Ser Phe Asn Asp Ile Ser Gln Asp Trp Arg Leu Arg His Phe Val<br>                   85                       90                   95 | 288 | |
| ggc tgg gtg tgg tac gaa cgg gag gtg atc ctg ccg gag cga tgg acc<br>Gly Trp Val Trp Tyr Glu Arg Glu Val Ile Leu Pro Glu Arg Trp Thr<br>                  100                  105                 110 | 336 | |
| cag gac ctg cgc aca aga gtg gtg ctg agg att ggc agt gcc cat tcc<br>Gln Asp Leu Arg Thr Arg Val Val Leu Arg Ile Gly Ser Ala His Ser<br>                 115                  120                 125 | 384 | |
| tat gcc atc gtg tgg gtg aat ggg gtc gac acg cta gag cat gag ggg<br>Tyr Ala Ile Val Trp Val Asn Gly Val Asp Thr Leu Glu His Glu Gly<br>130                      135                  140 | 432 | |
| ggc tac ctc ccc ttc gag gcc gac atc agc aac ctg gtc cag gtg ggg<br>Gly Tyr Leu Pro Phe Glu Ala Asp Ile Ser Asn Leu Val Gln Val Gly<br>145                      150                  155                 160 | 480 | |
| ccc ctg ccc tcc cgg ctc cga atc act atc gcc atc aac aac aca ctc<br>Pro Leu Pro Ser Arg Leu Arg Ile Thr Ile Ala Ile Asn Asn Thr Leu<br>                 165                  170                 175 | 528 | |
| acc ccc acc acc ctg cca cca ggg acc atc caa tac ctg act gac acc<br>Thr Pro Thr Thr Leu Pro Pro Gly Thr Ile Gln Tyr Leu Thr Asp Thr<br>                  180                  185                 190 | 576 | |
| tcc aag tat ccc aag ggt tac ttt gtc cag aac aca tat ttt gac ttt<br>Ser Lys Tyr Pro Lys Gly Tyr Phe Val Gln Asn Thr Tyr Phe Asp Phe<br>                 195                  200                 205 | 624 | |
| ttc aac tac gct gga ctg cag cgg tct gta ctt ctg tac acg aca ccc<br>Phe Asn Tyr Ala Gly Leu Gln Arg Ser Val Leu Leu Tyr Thr Thr Pro<br>210                      215                  220 | 672 | |
| acc acc tac atc gat gac atc acc gtc acc acc agc gtg gag caa gac<br>Thr Thr Tyr Ile Asp Asp Ile Thr Val Thr Thr Ser Val Glu Gln Asp<br>225                      230                  235                 240 | 720 | |
| agt ggg ctg gtg aat tac cag atc tct gtc aag ggc agt aac ctg ttc<br>Ser Gly Leu Val Asn Tyr Gln Ile Ser Val Lys Gly Ser Asn Leu Phe<br>                 245                  250                 255 | 768 | |
| aag ttg gaa gtg cgt ctt ttg gat gca gaa aac aaa gtc gtg gcg aat<br>Lys Leu Glu Val Arg Leu Leu Asp Ala Glu Asn Lys Val Val Ala Asn<br>                 260                  265                 270 | 816 | |
| ggg act ggg acc cag ggc caa ctt aag gtg cca ggt gtc agc ctc tgg<br>Gly Thr Gly Thr Gln Gly Gln Leu Lys Val Pro Gly Val Ser Leu Trp<br>275                      280                  285 | 864 | |
| tgg ccg tac ctg atg cac gaa cgc cct gcc tat ctg tat tca ttg gag<br>Trp Pro Tyr Leu Met His Glu Arg Pro Ala Tyr Leu Tyr Ser Leu Glu<br>                 290                  295                 300 | 912 | |
| gtg cag ctg act gca cag acg tca ctg ggg cct gtg tct gac ttc tac<br>Val Gln Leu Thr Ala Gln Thr Ser Leu Gly Pro Val Ser Asp Phe Tyr<br>305                      310                  315                 320 | 960 | |
| aca ctc cct gtg ggg atc cgc act gtg gct gtc acc aag agc cag ttc<br>Thr Leu Pro Val Gly Ile Arg Thr Val Ala Val Thr Lys Ser Gln Phe | 1008 | |

```
                    325                 330                 335
ctc atc aat ggg aaa cct ttc tat ttc cac ggt gtc aac aag cat gag    1056
Leu Ile Asn Gly Lys Pro Phe Tyr Phe His Gly Val Asn Lys His Glu
            340                 345                 350 gat gcg gac atc cga ggg aag ggc ttc gac tgg ccg ctg ctg gtg aag    1104
Asp Ala Asp Ile Arg Gly Lys Gly Phe Asp Trp Pro Leu Leu Val Lys
            355                 360                 365 gac ttc aac ctg ctt cgc tgg ctt ggt gcc aac gct ttc cgt acc agc    1152
Asp Phe Asn Leu Leu Arg Trp Leu Gly Ala Asn Ala Phe Arg Thr Ser
370                 375                 380 cac tac ccc tat gca gag gaa gtg atg cag atg tgt gac cgc tat ggg    1200
His Tyr Pro Tyr Ala Glu Glu Val Met Gln Met Cys Asp Arg Tyr Gly
385                 390                 395                 400 att gtg gtc atc gat gag tgt ccc ggc gtg ggc ctg gcg ctg ccg cag    1248
Ile Val Val Ile Asp Glu Cys Pro Gly Val Gly Leu Ala Leu Pro Gln
                405                 410                 415 ttc ttc aac aac gtt tct ctg cat cac cac atg cag gtg atg gaa gaa    1296
Phe Phe Asn Asn Val Ser Leu His His His Met Gln Val Met Glu Glu
            420                 425                 430 gtg gtg cgt agg gac aag aac cac ccc gcg gtc gtg atg tgg tct gtg    1344
Val Val Arg Arg Asp Lys Asn His Pro Ala Val Val Met Trp Ser Val
        435                 440                 445 gcc aac gag cct gcg tcc cac cta gaa tct gct ggc tac tac ttg aag    1392
Ala Asn Glu Pro Ala Ser His Leu Glu Ser Ala Gly Tyr Tyr Leu Lys
    450                 455                 460 atg gtg atc gct cac acc aaa tcc ttg gac ccc tcc cgg cct gtg acc    1440
Met Val Ile Ala His Thr Lys Ser Leu Asp Pro Ser Arg Pro Val Thr
465                 470                 475                 480 ttt gtg agc aac tct aac tat gca gca gac aag ggg gct ccg tat gtg    1488
Phe Val Ser Asn Ser Asn Tyr Ala Ala Asp Lys Gly Ala Pro Tyr Val
                485                 490                 495 gat gtg atc tgt ttg aac agc tac tac tct tgg tat cac gac tac ggg    1536
Asp Val Ile Cys Leu Asn Ser Tyr Tyr Ser Trp Tyr His Asp Tyr Gly
            500                 505                 510 cac ctg gag ttg att cag ctg cag ctg gcc acc cag ttt gag aac tgg    1584
His Leu Glu Leu Ile Gln Leu Gln Leu Ala Thr Gln Phe Glu Asn Trp
        515                 520                 525 tat aag aag tat cag aag ccc att att cag agc gag tat gga gca gaa    1632
Tyr Lys Lys Tyr Gln Lys Pro Ile Ile Gln Ser Glu Tyr Gly Ala Glu
    530                 535                 540 acg att gca ggg ttt cac cag gat cca cct ctg atg ttc act gaa gag    1680
Thr Ile Ala Gly Phe His Gln Asp Pro Pro Leu Met Phe Thr Glu Glu
545                 550                 555                 560 tac cag aaa agt ctg cta gag cag tac cat ctg ggt ctg gat caa aaa    1728
Tyr Gln Lys Ser Leu Leu Glu Gln Tyr His Leu Gly Leu Asp Gln Lys
                565                 570                 575 cgc aga aaa tat gtg gtt gga gag ctc att tgg aat ttt gcc gat ttc    1776
Arg Arg Lys Tyr Val Val Gly Glu Leu Ile Trp Asn Phe Ala Asp Phe
            580                 585                 590 atg act gaa cag tca ccg acg aga gtg ctg ggg aat aaa aag ggg atc    1824
Met Thr Glu Gln Ser Pro Thr Arg Val Leu Gly Asn Lys Lys Gly Ile
        595                 600                 605 ttc act cgg cag aga caa cca aaa agt gca gcg ttc ctt ttg cga gag    1872
Phe Thr Arg Gln Arg Gln Pro Lys Ser Ala Ala Phe Leu Leu Arg Glu
    610                 615                 620 aga tac tgg aag att gcc aat gaa acc agg tat ccc cac tca gta gcc    1920
Arg Tyr Trp Lys Ile Ala Asn Glu Thr Arg Tyr Pro His Ser Val Ala
625                 630                 635                 640 aag tca caa tgt ttg gaa aac agc ccg ttt act tga                    1956
Lys Ser Gln Cys Leu Glu Asn Ser Pro Phe Thr
```

-continued

```
Lys Ser Gln Cys Leu Glu Asn Ser Pro Phe Thr
                645                 650

<210> SEQ ID NO 2
<211> LENGTH: 651
<212> TYPE: PRT
<213> ORGANISM: Homo sapiens

<400> SEQUENCE: 2

Met Ala Arg Gly Ser Ala Val Ala Trp Ala Leu Gly Pro Leu Leu
  1               5                  10                  15

Trp Gly Cys Ala Leu Gly Leu Gln Gly Gly Met Leu Tyr Pro Gln Glu
                 20                  25                  30

Ser Pro Ser Arg Glu Cys Lys Glu Leu Asp Gly Leu Trp Ser Phe Arg
             35                  40                  45

Ala Asp Phe Ser Asp Asn Arg Arg Gly Phe Glu Glu Gln Trp Tyr
         50                  55                  60

Arg Arg Pro Leu Trp Glu Ser Gly Pro Thr Val Asp Met Pro Val Pro
 65                  70                  75                  80

Ser Ser Phe Asn Asp Ile Ser Gln Asp Trp Arg Leu Arg His Phe Val
                 85                  90                  95

Gly Trp Val Trp Tyr Glu Arg Glu Val Ile Leu Pro Glu Arg Trp Thr
                100                 105                 110

Gln Asp Leu Arg Thr Arg Val Val Leu Arg Ile Gly Ser Ala His Ser
            115                 120                 125

Tyr Ala Ile Val Trp Val Asn Gly Val Asp Thr Leu Glu His Glu Gly
        130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
                180                 185                 190

Ser Lys Tyr Pro Lys Gly Tyr Phe Val Gln Asn Thr Tyr Phe Asp Phe
            195                 200                 205

Phe Asn Tyr Ala Gly Leu Gln Arg Ser Val Leu Leu Tyr Thr Thr Pro
        210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
                260                 265                 270

Gly Thr Gly Thr Gln Gly Gln Leu Lys Val Pro Gly Val Ser Leu Trp
            275                 280                 285

Trp Pro Tyr Leu Met His Glu Arg Pro Ala Tyr Leu Tyr Ser Leu Glu
        290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
                340                 345                 350

Asp Ala Asp Ile Arg Gly Lys Gly Phe Asp Trp Pro Leu Leu Val Lys
            355                 360                 365
```

```
Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
                420                 425                 430

Val Val Arg Arg Asp Lys Asn His Pro Ala Val Val Met Trp Ser Val
            435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
                500                 505                 510

His Leu Glu Leu Ile Gln Leu Gln Leu Ala Thr Gln Phe Glu Asn Trp
            515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
            595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Pro Phe Thr
                645                 650

<210> SEQ ID NO 3
<211> LENGTH: 1947
<212> TYPE: DNA
<213> ORGANISM: Mus musculus
<220> FEATURE:
<221> NAME/KEY: CDS
<222> LOCATION: (1)..(1947)

<400> SEQUENCE: 3 atg tcc cta aaa tgg agt gcg tgt tgg gtc gcg ctg ggc cag ctg ctg      48
Met Ser Leu Lys Trp Ser Ala Cys Trp Val Ala Leu Gly Gln Leu Leu
  1               5                  10                  15 tgc agc tgc gcg ctg gct ctg aag ggc ggg atg ctg ttc ccg aag gag      96
Cys Ser Cys Ala Leu Ala Leu Lys Gly Gly Met Leu Phe Pro Lys Glu
             20                  25                  30 agc ccg tcg cgg gag ctc aag gcg ctg gac gga ctg tgg cac ttc cgc     144
Ser Pro Ser Arg Glu Leu Lys Ala Leu Asp Gly Leu Trp His Phe Arg
         35                  40                  45 gcc gac ctc tcg aac aac cgg ctg cag ggt ttc gag cag caa tgg tac     192
```

-continued

| | | |
|---|---|---|
| Ala Asp Leu Ser Asn Asn Arg Leu Gln Gly Phe Glu Gln Gln Trp Tyr<br>50 55 60 | | |
| cgg cag ccg cta cgg gag tcg ggc cca gtc ttg gac atg cct gtc cct<br>Arg Gln Pro Leu Arg Glu Ser Gly Pro Val Leu Asp Met Pro Val Pro<br>65 70 75 80 | | 240 |
| tct agc ttc aat gac atc acc caa gaa gca gcc ctt cgg gac ttt att<br>Ser Ser Phe Asn Asp Ile Thr Gln Glu Ala Ala Leu Arg Asp Phe Ile<br>85 90 95 | | 288 |
| ggc tgg gtg tgg tat gaa cgg gaa gca atc ctg cca cgg cga tgg acc<br>Gly Trp Val Trp Tyr Glu Arg Glu Ala Ile Leu Pro Arg Arg Trp Thr<br>100 105 110 | | 336 |
| caa gat acc gac atg aga gtg gtg ttg agg atc aac agt gcc cat tat<br>Gln Asp Thr Asp Met Arg Val Val Leu Arg Ile Asn Ser Ala His Tyr<br>115 120 125 | | 384 |
| tat gca gtt gtg tgg gtg aat ggg att cat gtg gtg gaa cat gag gga<br>Tyr Ala Val Val Trp Val Asn Gly Ile His Val Val Glu His Glu Gly<br>130 135 140 | | 432 |
| ggt cac ctc ccc ttt gag gct gac att agc aag ctg gtc cag agt ggg<br>Gly His Leu Pro Phe Glu Ala Asp Ile Ser Lys Leu Val Gln Ser Gly<br>145 150 155 160 | | 480 |
| ccc ctg acc acc tgc cgg atc acg att gcc atc aac aac aca ctg acc<br>Pro Leu Thr Thr Cys Arg Ile Thr Ile Ala Ile Asn Asn Thr Leu Thr<br>165 170 175 | | 528 |
| cct cat acc ctt ccg ccg ggg acc atc gtc tac aag act gac acc tcc<br>Pro His Thr Leu Pro Pro Gly Thr Ile Val Tyr Lys Thr Asp Thr Ser<br>180 185 190 | | 576 |
| atg tat ccc aag ggt tac ttt gtc cag gac aca agc ttt gac ttc ttc<br>Met Tyr Pro Lys Gly Tyr Phe Val Gln Asp Thr Ser Phe Asp Phe Phe<br>195 200 205 | | 624 |
| aac tat gcg gga ctg cat cga tct gtg gtc ctc tat acc acc cct acc<br>Asn Tyr Ala Gly Leu His Arg Ser Val Val Leu Tyr Thr Thr Pro Thr<br>210 215 220 | | 672 |
| act tac atc gat gat atc act gtg atc act aat gtg gag caa gac atc<br>Thr Tyr Ile Asp Asp Ile Thr Val Ile Thr Asn Val Glu Gln Asp Ile<br>225 230 235 240 | | 720 |
| ggg ctg gtg acc tac tgg att tct gtg cag ggc agt gaa cat ttc cag<br>Gly Leu Val Thr Tyr Trp Ile Ser Val Gln Gly Ser Glu His Phe Gln<br>245 250 255 | | 768 |
| cta gaa gtg caa ctt ttg gat gag ggt ggc aaa gtc gtg gcc cat ggg<br>Leu Glu Val Gln Leu Leu Asp Glu Gly Gly Lys Val Val Ala His Gly<br>260 265 270 | | 816 |
| aca ggg aac cag ggt caa ctt cag gtt ccc agt gcc aac ctc tgg tgg<br>Thr Gly Asn Gln Gly Gln Leu Gln Val Pro Ser Ala Asn Leu Trp Trp<br>275 280 285 | | 864 |
| cct tac ctg atg cat gag cat cca gcc tac atg tac tcc ttg gag gtg<br>Pro Tyr Leu Met His Glu His Pro Ala Tyr Met Tyr Ser Leu Glu Val<br>290 295 300 | | 912 |
| aag gtg aca aca act gag tct gtg act gac tac tac acc ctt cct atc<br>Lys Val Thr Thr Thr Glu Ser Val Thr Asp Tyr Tyr Thr Leu Pro Ile<br>305 310 315 320 | | 960 |
| ggg att cga aca gtg gct gtc aca aag agc aag ttc ctc ata aac ggg<br>Gly Ile Arg Thr Val Ala Val Thr Lys Ser Lys Phe Leu Ile Asn Gly<br>325 330 335 | | 1008 |
| aag ccc ttc tat ttc caa ggg gtc aat aag cac gag gat tca gat atc<br>Lys Pro Phe Tyr Phe Gln Gly Val Asn Lys His Glu Asp Ser Asp Ile<br>340 345 350 | | 1056 |
| cga ggg aaa ggc ttc gac tgg ccg ctg ctg gta aag gat ttc aac ctg<br>Arg Gly Lys Gly Phe Asp Trp Pro Leu Leu Val Lys Asp Phe Asn Leu<br>355 360 365 | | 1104 |

| | | | | | | | | | | | | | | |
|---|---|---|---|---|---|---|---|---|---|---|---|---|---|---|
| ctc | cgt | tgg | ctc | ggg | gca | aat | tcc | ttt | cgt | acc | agc | cac | tat ccc tac | 1152 |
| Leu | Arg | Trp | Leu | Gly | Ala | Asn | Ser | Phe | Arg | Thr | Ser | His | Tyr Pro Tyr | |
| | 370 | | | | 375 | | | | | 380 | | | | |

| | | | | | | | | | | | | | | |
|---|---|---|---|---|---|---|---|---|---|---|---|---|---|---|
| tca | gag | gag | gta | ctt | cag | ctc | tgt | gac | cga | tac | ggg | att | gtg gtc atc | 1200 |
| Ser | Glu | Glu | Val | Leu | Gln | Leu | Cys | Asp | Arg | Tyr | Gly | Ile | Val Val Ile | |
| 385 | | | | | 390 | | | | | 395 | | | 400 | |

| | | | | | | | | | | | | | | |
|---|---|---|---|---|---|---|---|---|---|---|---|---|---|---|
| gat | gag | tgt | ccc | ggt | gtg | ggc | att | gtg | cta | cct | cag | agt | ttt ggc aac | 1248 |
| Asp | Glu | Cys | Pro | Gly | Val | Gly | Ile | Val | Leu | Pro | Gln | Ser | Phe Gly Asn | |
| | | | | 405 | | | | | 410 | | | | 415 | |

| | | | | | | | | | | | | | | |
|---|---|---|---|---|---|---|---|---|---|---|---|---|---|---|
| gag | tca | ctt | cgg | cac | cac | cta | gag | gtg | atg | gag | gag | ctg | gtt cgc cgg | 1296 |
| Glu | Ser | Leu | Arg | His | His | Leu | Glu | Val | Met | Glu | Glu | Leu | Val Arg Arg | |
| | | | 420 | | | | | 425 | | | | | 430 | |

| | | | | | | | | | | | | | | |
|---|---|---|---|---|---|---|---|---|---|---|---|---|---|---|
| gac | aaa | aat | cac | cct | gcg | gtt | gtg | atg | tgg | tct | gtg | gcc | aat gag cct | 1344 |
| Asp | Lys | Asn | His | Pro | Ala | Val | Val | Met | Trp | Ser | Val | Ala | Asn Glu Pro | |
| | | | 435 | | | | | 440 | | | | | 445 | |

| | | | | | | | | | | | | | | |
|---|---|---|---|---|---|---|---|---|---|---|---|---|---|---|
| tcc | tct | gct | ctg | aaa | ccc | gcc | gca | tat | tac | ttt | aag | acg | ctg atc acc | 1392 |
| Ser | Ser | Ala | Leu | Lys | Pro | Ala | Ala | Tyr | Tyr | Phe | Lys | Thr | Leu Ile Thr | |
| | 450 | | | | | 455 | | | | | 460 | | | |

| | | | | | | | | | | | | | | |
|---|---|---|---|---|---|---|---|---|---|---|---|---|---|---|
| cac | acc | aaa | gcc | ctg | gac | ctc | acc | cgt | ccc | gtg | acc | ttt | gtg agc aac | 1440 |
| His | Thr | Lys | Ala | Leu | Asp | Leu | Thr | Arg | Pro | Val | Thr | Phe | Val Ser Asn | |
| 465 | | | | | 470 | | | | | 475 | | | | 480 |

| | | | | | | | | | | | | | | |
|---|---|---|---|---|---|---|---|---|---|---|---|---|---|---|
| gcc | aaa | tat | gat | gca | gac | ctg | ggg | gcc | ccg | tac | gtg | gat | gtt atc tgt | 1488 |
| Ala | Lys | Tyr | Asp | Ala | Asp | Leu | Gly | Ala | Pro | Tyr | Val | Asp | Val Ile Cys | |
| | | | | 485 | | | | | 490 | | | | | 495 |

| | | | | | | | | | | | | | | |
|---|---|---|---|---|---|---|---|---|---|---|---|---|---|---|
| gta | aac | agc | tac | ttt | tct | tgg | tat | cat | gac | tat | ggg | cat | ttg gag gtg | 1536 |
| Val | Asn | Ser | Tyr | Phe | Ser | Trp | Tyr | His | Asp | Tyr | Gly | His | Leu Glu Val | |
| | | | 500 | | | | | 505 | | | | | 510 | |

| | | | | | | | | | | | | | | |
|---|---|---|---|---|---|---|---|---|---|---|---|---|---|---|
| att | cag | cca | cag | ctg | aat | agc | cag | ttt | gag | aac | tgg | tat | aag acg cat | 1584 |
| Ile | Gln | Pro | Gln | Leu | Asn | Ser | Gln | Phe | Glu | Asn | Trp | Tyr | Lys Thr His | |
| | | | 515 | | | | | 520 | | | | | 525 | |

| | | | | | | | | | | | | | | |
|---|---|---|---|---|---|---|---|---|---|---|---|---|---|---|
| cag | aag | ccg | att | atc | cag | agc | gag | tat | gga | gca | gac | gca | atc cca ggg | 1632 |
| Gln | Lys | Pro | Ile | Ile | Gln | Ser | Glu | Tyr | Gly | Ala | Asp | Ala | Ile Pro Gly | |
| | 530 | | | | | 535 | | | | | 540 | | | |

| | | | | | | | | | | | | | | |
|---|---|---|---|---|---|---|---|---|---|---|---|---|---|---|
| atc | cac | gag | gac | ccg | cct | cgc | atg | ttc | agt | gag | gag | tac | cag aag gct | 1680 |
| Ile | His | Glu | Asp | Pro | Pro | Arg | Met | Phe | Ser | Glu | Glu | Tyr | Gln Lys Ala | |
| 545 | | | | | 550 | | | | | 555 | | | | 560 |

| | | | | | | | | | | | | | | |
|---|---|---|---|---|---|---|---|---|---|---|---|---|---|---|
| gtt | ctg | gag | aat | tac | cat | tca | gtt | ctg | gat | cag | aaa | cgt | aaa gaa tac | 1728 |
| Val | Leu | Glu | Asn | Tyr | His | Ser | Val | Leu | Asp | Gln | Lys | Arg | Lys Glu Tyr | |
| | | | | 565 | | | | | 570 | | | | | 575 |

| | | | | | | | | | | | | | | |
|---|---|---|---|---|---|---|---|---|---|---|---|---|---|---|
| gtg | gtc | gga | gag | ctc | atc | tgg | aat | ttc | gcc | gac | ttc | atg | acg aac cag | 1776 |
| Val | Val | Gly | Glu | Leu | Ile | Trp | Asn | Phe | Ala | Asp | Phe | Met | Thr Asn Gln | |
| | | | 580 | | | | | 585 | | | | | 590 | |

| | | | | | | | | | | | | | | |
|---|---|---|---|---|---|---|---|---|---|---|---|---|---|---|
| tca | ccg | ctg | aga | gta | atc | gga | aac | aag | aag | ggg | atc | ttc | act cgc cag | 1824 |
| Ser | Pro | Leu | Arg | Val | Ile | Gly | Asn | Lys | Lys | Gly | Ile | Phe | Thr Arg Gln | |
| | | | 595 | | | | | 600 | | | | | 605 | |

| | | | | | | | | | | | | | | |
|---|---|---|---|---|---|---|---|---|---|---|---|---|---|---|
| aga | cag | ccc | aaa | act | tcg | gcc | ttt | att | ttg | cga | gag | aga | tac tgg agg | 1872 |
| Arg | Gln | Pro | Lys | Thr | Ser | Ala | Phe | Ile | Leu | Arg | Glu | Arg | Tyr Trp Arg | |
| | 610 | | | | | 615 | | | | | 620 | | | |

| | | | | | | | | | | | | | | |
|---|---|---|---|---|---|---|---|---|---|---|---|---|---|---|
| att | gcc | aac | gaa | acc | gga | ggt | cac | ggt | tca | ggg | ccg | aga | acc cag tgt | 1920 |
| Ile | Ala | Asn | Glu | Thr | Gly | Gly | His | Gly | Ser | Gly | Pro | Arg | Thr Gln Cys | |
| 625 | | | | | 630 | | | | | 635 | | | | 640 |

| | | | | | | | |
|---|---|---|---|---|---|---|---|
| ttc | gga | agc | aga | ccg | ttc | acg ttc taa | 1947 |
| Phe | Gly | Ser | Arg | Pro | Phe | Thr Phe | |
| | | | | | | 645 | |

<210> SEQ ID NO 4
<211> LENGTH: 648
<212> TYPE: PRT
<213> ORGANISM: Mus musculus

<400> SEQUENCE: 4

```
Met Ser Leu Lys Trp Ser Ala Cys Trp Val Ala Leu Gly Gln Leu Leu
 1               5                  10                  15

Cys Ser Cys Ala Leu Ala Leu Lys Gly Gly Met Leu Phe Pro Lys Glu
            20                  25                  30

Ser Pro Ser Arg Glu Leu Lys Ala Leu Asp Gly Leu Trp His Phe Arg
        35                  40                  45

Ala Asp Leu Ser Asn Asn Arg Leu Gln Gly Phe Glu Gln Gln Trp Tyr
    50                  55                  60

Arg Gln Pro Leu Arg Glu Ser Gly Pro Val Leu Asp Met Pro Val Pro
65                  70                  75                  80

Ser Ser Phe Asn Asp Ile Thr Gln Glu Ala Ala Leu Arg Asp Phe Ile
                85                  90                  95

Gly Trp Val Trp Tyr Glu Arg Glu Ala Ile Leu Pro Arg Arg Trp Thr
                100                 105                 110

Gln Asp Thr Asp Met Arg Val Leu Arg Ile Asn Ser Ala His Tyr
                115                 120                 125

Tyr Ala Val Val Trp Val Asn Gly Ile His Val Glu His Glu Gly
        130                 135                 140

Gly His Leu Pro Phe Glu Ala Asp Ile Ser Lys Leu Val Gln Ser Gly
145                 150                 155                 160

Pro Leu Thr Thr Cys Arg Ile Thr Ile Ala Ile Asn Asn Thr Leu Thr
                165                 170                 175

Pro His Thr Leu Pro Pro Gly Thr Ile Val Tyr Lys Thr Asp Thr Ser
                180                 185                 190

Met Tyr Pro Lys Gly Tyr Phe Val Gln Asp Thr Ser Phe Asp Phe Phe
        195                 200                 205

Asn Tyr Ala Gly Leu His Arg Ser Val Val Leu Tyr Thr Thr Pro Thr
210                 215                 220

Thr Tyr Ile Asp Asp Ile Thr Val Ile Thr Asn Val Glu Gln Asp Ile
225                 230                 235                 240

Gly Leu Val Thr Tyr Trp Ile Ser Val Gln Gly Ser Glu His Phe Gln
                245                 250                 255

Leu Glu Val Gln Leu Leu Asp Glu Gly Gly Lys Val Val Ala His Gly
                260                 265                 270

Thr Gly Asn Gln Gly Gln Leu Gln Val Pro Ser Ala Asn Leu Trp Trp
        275                 280                 285

Pro Tyr Leu Met His Glu His Pro Ala Tyr Met Tyr Ser Leu Glu Val
        290                 295                 300

Lys Val Thr Thr Thr Glu Ser Val Thr Asp Tyr Tyr Thr Leu Pro Ile
305                 310                 315                 320

Gly Ile Arg Thr Val Ala Val Thr Lys Ser Lys Phe Leu Ile Asn Gly
                325                 330                 335

Lys Pro Phe Tyr Phe Gln Gly Val Asn Lys His Glu Asp Ser Asp Ile
                340                 345                 350

Arg Gly Lys Gly Phe Asp Trp Pro Leu Leu Val Lys Asp Phe Asn Leu
                355                 360                 365

Leu Arg Trp Leu Gly Ala Asn Ser Phe Arg Thr Ser His Tyr Pro Tyr
        370                 375                 380

Ser Glu Glu Val Leu Gln Leu Cys Asp Arg Tyr Gly Ile Val Val Ile
385                 390                 395                 400

Asp Glu Cys Pro Gly Val Gly Ile Val Leu Pro Gln Ser Phe Gly Asn
                405                 410                 415
```

-continued

```
Glu Ser Leu Arg His His Leu Glu Val Met Glu Glu Leu Val Arg Arg
            420                 425                 430

Asp Lys Asn His Pro Ala Val Val Met Trp Ser Val Ala Asn Glu Pro
            435                 440                 445

Ser Ser Ala Leu Lys Pro Ala Ala Tyr Tyr Phe Lys Thr Leu Ile Thr
450                 455                 460

His Thr Lys Ala Leu Asp Leu Thr Arg Pro Val Thr Phe Val Ser Asn
465                 470                 475                 480

Ala Lys Tyr Asp Ala Asp Leu Gly Ala Pro Tyr Val Asp Val Ile Cys
                485                 490                 495

Val Asn Ser Tyr Phe Ser Trp Tyr His Asp Tyr Gly His Leu Glu Val
            500                 505                 510

Ile Gln Pro Gln Leu Asn Ser Gln Phe Glu Asn Trp Tyr Lys Thr His
            515                 520                 525

Gln Lys Pro Ile Ile Gln Ser Gly Tyr Gly Ala Asp Ala Ile Pro Gly
            530                 535                 540

Ile His Glu Asp Pro Pro Arg Met Phe Ser Glu Glu Tyr Gln Lys Ala
545                 550                 555                 560

Val Leu Glu Asn Tyr His Ser Val Leu Asp Gln Lys Arg Lys Glu Tyr
                565                 570                 575

Val Val Gly Glu Leu Ile Trp Asn Phe Ala Asp Phe Met Thr Asn Gln
            580                 585                 590

Ser Pro Leu Arg Val Ile Gly Asn Lys Lys Gly Ile Phe Thr Arg Gln
            595                 600                 605

Arg Gln Pro Lys Thr Ser Ala Phe Ile Leu Arg Glu Arg Tyr Trp Arg
            610                 615                 620

Ile Ala Asn Glu Thr Gly Gly His Gly Ser Gly Pro Arg Thr Gln Cys
625                 630                 635                 640

Phe Gly Ser Arg Pro Phe Thr Phe
                645
```

<210> SEQ ID NO 5
<211> LENGTH: 1551
<212> TYPE: DNA
<213> ORGANISM: Homo sapiens
<220> FEATURE:
<221> NAME/KEY: CDS
<222> LOCATION: (1)..(1551)

<400> SEQUENCE: 5

```
atg gct ggc agc ctc aca ggt ttg ctt cta ctt cag gca gtg tcg tgg      48
Met Ala Gly Ser Leu Thr Gly Leu Leu Leu Leu Gln Ala Val Ser Trp
1               5                   10                  15 gca tca ggt gcc cgc ccc tgc atc cct aaa agc ttc ggc tac agc tcg      96
Ala Ser Gly Ala Arg Pro Cys Ile Pro Lys Ser Phe Gly Tyr Ser Ser
            20                  25                  30 gtg gtg tgt gtc tgc aat gcc aca tac tgt gac tcc ttt gac ccc ccg     144
Val Val Cys Val Cys Asn Ala Thr Tyr Cys Asp Ser Phe Asp Pro Pro
        35                  40                  45 acc ttt cct gcc ctt ggt acc ttc agc cgc tat gag agt aca cgc agt     192
Thr Phe Pro Ala Leu Gly Thr Phe Ser Arg Tyr Glu Ser Thr Arg Ser
    50                  55                  60 ggg cga cgg atg gag ctg agt atg ggg ccc atc cag gct aat cac acg     240
Gly Arg Arg Met Glu Leu Ser Met Gly Pro Ile Gln Ala Asn His Thr
65                  70                  75                  80 ggc aca ggc ctg cta ctg acc ctg cag cca gaa cag aag ttc cag aaa     288
Gly Thr Gly Leu Leu Leu Thr Leu Gln Pro Glu Gln Lys Phe Gln Lys
                85                  90                  95
```

-continued

| | |
|---|---|
| gtg aag gga ttt gga ggg gcc atg aca gat gct gct gct ctc aac atc<br>Val Lys Gly Phe Gly Gly Ala Met Thr Asp Ala Ala Ala Leu Asn Ile<br>100                        105                      110 | 336 |
| ctt gcc ctg tca ccc cct gcc caa aat ttg cta ctt aaa tcg tac ttc<br>Leu Ala Leu Ser Pro Pro Ala Gln Asn Leu Leu Leu Lys Ser Tyr Phe<br>115                        120                      125 | 384 |
| tct gaa gaa gga atc gga tat aac atc atc cgg gta ccc atg gcc agc<br>Ser Glu Glu Gly Ile Gly Tyr Asn Ile Ile Arg Val Pro Met Ala Ser<br>130                        135                      140 | 432 |
| tgt gac ttc tcc atc cgc acc tac acc tat gca gac acc cct gat gat<br>Cys Asp Phe Ser Ile Arg Thr Tyr Thr Tyr Ala Asp Thr Pro Asp Asp<br>145                        150                      155                      160 | 480 |
| ttc cag ttg cac aac ttc agc ctc cca gag gaa gat acc aag ctc aag<br>Phe Gln Leu His Asn Phe Ser Leu Pro Glu Glu Asp Thr Lys Leu Lys<br>165                        170                      175 | 528 |
| ata ccc ctg att cac cga gcc ctg cag ttg gcc cag cgt ccc gtt tca<br>Ile Pro Leu Ile His Arg Ala Leu Gln Leu Ala Gln Arg Pro Val Ser<br>180                        185                      190 | 576 |
| ctc ctt gcc agc ccc tgg aca tca ccc act tgg ctc aag acc aat gga<br>Leu Leu Ala Ser Pro Trp Thr Ser Pro Thr Trp Leu Lys Thr Asn Gly<br>195                        200                      205 | 624 |
| gcg gtg aat ggg aag ggg tca ctc aag gga cag ccc gga gac atc tac<br>Ala Val Asn Gly Lys Gly Ser Leu Lys Gly Gln Pro Gly Asp Ile Tyr<br>210                        215                      220 | 672 |
| cac cag acc tgg gcc aga tac ttt gtg aag ttc ctg gat gcc tat gct<br>His Gln Thr Trp Ala Arg Tyr Phe Val Lys Phe Leu Asp Ala Tyr Ala<br>225                        230                      235                      240 | 720 |
| gag cac aag tta cag ttc tgg gca gtg aca gct gaa aat gag cct tct<br>Glu His Lys Leu Gln Phe Trp Ala Val Thr Ala Glu Asn Glu Pro Ser<br>245                        250                      255 | 768 |
| gct ggg ctg ttg agt gga tac ccc ttc cag tgc ctg ggc ttc acc cct<br>Ala Gly Leu Leu Ser Gly Tyr Pro Phe Gln Cys Leu Gly Phe Thr Pro<br>260                        265                      270 | 816 |
| gaa cat cag cga gac ttc att gcc cgt gac cta ggt cct acc ctc gcc<br>Glu His Gln Arg Asp Phe Ile Ala Arg Asp Leu Gly Pro Thr Leu Ala<br>275                        280                      285 | 864 |
| aac agt act cac cac aat gtc cgc cta ctc atg ctg gat gac caa cgc<br>Asn Ser Thr His His Asn Val Arg Leu Leu Met Leu Asp Asp Gln Arg<br>290                        295                      300 | 912 |
| ttg ctg ctg ccc cac tgg gca aag gtg gta ctg aca gac cca gaa gca<br>Leu Leu Leu Pro His Trp Ala Lys Val Val Leu Thr Asp Pro Glu Ala<br>305                        310                      315                      320 | 960 |
| gct aaa tat gtt cat ggc att gct gta cat tgg tac ctg gac ttt ctg<br>Ala Lys Tyr Val His Gly Ile Ala Val His Trp Tyr Leu Asp Phe Leu<br>325                        330                      335 | 1008 |
| gct cca gcc aaa gcc acc cta ggg gag aca cac cgc ctg ttc ccc aac<br>Ala Pro Ala Lys Ala Thr Leu Gly Glu Thr His Arg Leu Phe Pro Asn<br>340                        345                      350 | 1056 |
| acc atg ctc ttt gcc tca gag gcc tgt gtg ggc tcc aag ttc tgg gag<br>Thr Met Leu Phe Ala Ser Glu Ala Cys Val Gly Ser Lys Phe Trp Glu<br>355                        360                      365 | 1104 |
| cag agt gtg cgg cta ggc tcc tgg gat cga ggg atg cag tac agc cac<br>Gln Ser Val Arg Leu Gly Ser Trp Asp Arg Gly Met Gln Tyr Ser His<br>370                        375                      380 | 1152 |
| agc atc atc acg aac ctc ctg tac cat gtg gtc ggc tgg acc gac tgg<br>Ser Ile Ile Thr Asn Leu Leu Tyr His Val Val Gly Trp Thr Asp Trp<br>385                        390                      395                      400 | 1200 |
| aac ctt gcc ctg aac ccc gaa gga gga ccc aat tgg gtg cgt aac ttt<br>Asn Leu Ala Leu Asn Pro Glu Gly Gly Pro Asn Trp Val Arg Asn Phe | 1248 |

```
gtc gac agt ccc atc att gta gac atc acc aag gac acg ttt tac aaa    1296
Val Asp Ser Pro Ile Ile Val Asp Ile Thr Lys Asp Thr Phe Tyr Lys
            420                 425                 430 cag ccc atg ttc tac cac ctt ggc cac ttc agc aag ttc att cct gag    1344
Gln Pro Met Phe Tyr His Leu Gly His Phe Ser Lys Phe Ile Pro Glu
        435                 440                 445 ggc tcc cag aga gtg ggg ctg gtt gcc agt cag aag aac gac ctg gac    1392
Gly Ser Gln Arg Val Gly Leu Val Ala Ser Gln Lys Asn Asp Leu Asp
    450                 455                 460 gca gtg gca ctg atg cat ccc gat ggc tct gct gtt gtg gtc gtg cta    1440
Ala Val Ala Leu Met His Pro Asp Gly Ser Ala Val Val Val Val Leu
465                 470                 475                 480 aac cgc tcc tct aag gat gtg cct ctt acc atc aag gat cct gct gtg    1488
Asn Arg Ser Ser Lys Asp Val Pro Leu Thr Ile Lys Asp Pro Ala Val
                485                 490                 495 ggc ttc ctg gag aca atc tca cct ggc tac tcc att cac acc tac ctg    1536
Gly Phe Leu Glu Thr Ile Ser Pro Gly Tyr Ser Ile His Thr Tyr Leu
            500                 505                 510 tgg cat cgc cag tga                                                1551
Trp His Arg Gln
        515
```

<210> SEQ ID NO 6
<211> LENGTH: 516
<212> TYPE: PRT
<213> ORGANISM: Homo sapiens

<400> SEQUENCE: 6

```
Met Ala Gly Ser Leu Thr Gly Leu Leu Leu Leu Gln Ala Val Ser Trp
 1               5                  10                  15

Ala Ser Gly Ala Arg Pro Cys Ile Pro Lys Ser Phe Gly Tyr Ser Ser
                20                  25                  30

Val Val Cys Val Cys Asn Ala Thr Tyr Cys Asp Ser Phe Asp Pro Pro
            35                  40                  45

Thr Phe Pro Ala Leu Gly Thr Phe Ser Arg Tyr Glu Ser Thr Arg Ser
        50                  55                  60

Gly Arg Arg Met Glu Leu Ser Met Gly Pro Ile Gln Ala Asn His Thr
65                  70                  75                  80

Gly Thr Gly Leu Leu Leu Thr Leu Gln Pro Glu Gln Lys Phe Gln Lys
                85                  90                  95

Val Lys Gly Phe Gly Gly Ala Met Thr Asp Ala Ala Ala Leu Asn Ile
            100                 105                 110

Leu Ala Leu Ser Pro Pro Ala Gln Asn Leu Leu Leu Lys Ser Tyr Phe
        115                 120                 125

Ser Glu Glu Gly Ile Gly Tyr Asn Ile Ile Arg Val Pro Met Ala Ser
    130                 135                 140

Cys Asp Phe Ser Ile Arg Thr Tyr Thr Tyr Ala Asp Thr Pro Asp Asp
145                 150                 155                 160

Phe Gln Leu His Asn Phe Ser Leu Pro Glu Glu Asp Thr Lys Leu Lys
                165                 170                 175

Ile Pro Leu Ile His Arg Ala Leu Gln Leu Ala Gln Arg Pro Val Ser
            180                 185                 190

Leu Leu Ala Ser Pro Trp Thr Ser Pro Thr Trp Leu Lys Thr Asn Gly
        195                 200                 205

Ala Val Asn Gly Lys Gly Ser Leu Lys Gly Gln Pro Gly Asp Ile Tyr
    210                 215                 220
```

```
His Gln Thr Trp Ala Arg Tyr Phe Val Lys Phe Leu Asp Ala Tyr Ala
225                 230                 235                 240

Glu His Lys Leu Gln Phe Trp Ala Val Thr Ala Glu Asn Glu Pro Ser
            245                 250                 255

Ala Gly Leu Leu Ser Gly Tyr Pro Phe Gln Cys Leu Gly Phe Thr Pro
            260                 265                 270

Glu His Gln Arg Asp Phe Ile Ala Arg Asp Leu Gly Pro Thr Leu Ala
        275                 280                 285

Asn Ser Thr His His Asn Val Arg Leu Leu Met Leu Asp Asp Gln Arg
    290                 295                 300

Leu Leu Leu Pro His Trp Ala Lys Val Leu Thr Asp Pro Glu Ala
305                 310                 315                 320

Ala Lys Tyr Val His Gly Ile Ala Val His Trp Tyr Leu Asp Phe Leu
            325                 330                 335

Ala Pro Ala Lys Ala Thr Leu Gly Glu Thr His Arg Leu Phe Pro Asn
        340                 345                 350

Thr Met Leu Phe Ala Ser Glu Ala Cys Val Gly Ser Lys Phe Trp Glu
    355                 360                 365

Gln Ser Val Arg Leu Gly Ser Trp Asp Arg Gly Met Gln Tyr Ser His
370                 375                 380

Ser Ile Ile Thr Asn Leu Leu Tyr His Val Val Gly Trp Thr Asp Trp
385                 390                 395                 400

Asn Leu Ala Leu Asn Pro Glu Gly Gly Pro Asn Trp Val Arg Asn Phe
            405                 410                 415

Val Asp Ser Pro Ile Ile Val Asp Ile Thr Lys Asp Thr Phe Tyr Lys
        420                 425                 430

Gln Pro Met Phe Tyr His Leu Gly His Phe Ser Lys Phe Ile Pro Glu
    435                 440                 445

Gly Ser Gln Arg Val Gly Leu Val Ala Ser Gln Lys Asn Asp Leu Asp
450                 455                 460

Ala Val Ala Leu Met His Pro Asp Gly Ser Ala Val Val Val Val Leu
465                 470                 475                 480

Asn Arg Ser Ser Lys Asp Val Pro Leu Thr Ile Lys Asp Pro Ala Val
            485                 490                 495

Gly Phe Leu Glu Thr Ile Ser Pro Gly Tyr Ser Ile His Thr Tyr Leu
        500                 505                 510

Trp His Arg Gln
        515

<210> SEQ ID NO 7
<211> LENGTH: 1611
<212> TYPE: DNA
<213> ORGANISM: Homo sapiens
<220> FEATURE:
<221> NAME/KEY: CDS
<222> LOCATION: (1)..(1611)

<400> SEQUENCE: 7 atg gag ttt tca agt cct tcc aga gag gaa tgt ccc aag cct ttg aat     48
Met Glu Phe Ser Ser Pro Ser Arg Glu Glu Cys Pro Lys Pro Leu Asn
  1               5                  10                  15 gac cct gag ggg atg gct ggc agc ctc aca ggt ttg ctt cta ctt cag     96
Asp Pro Glu Gly Met Ala Gly Ser Leu Thr Gly Leu Leu Leu Leu Gln
             20                  25                  30 gca gtg tcg tgg gca tca ggt gcc cgc ccc tgc atc cct aaa agc ttc    144
Ala Val Ser Trp Ala Ser Gly Ala Arg Pro Cys Ile Pro Lys Ser Phe
```

```
                    35                    40                        45
ggc  tac  agc  tcg  gtg  gtg  tgt  gtc  tgc  aat  gcc  aca  tac  tgt  gac  tcc       192
Gly  Tyr  Ser  Ser  Val  Val  Cys  Val  Cys  Asn  Ala  Thr  Tyr  Cys  Asp  Ser
          50                        55                        60 ttt  gac  ccc  ccg  acc  ttt  cct  gcc  ctt  ggt  acc  ttc  agc  cgc  tat  gag       240
Phe  Asp  Pro  Pro  Thr  Phe  Pro  Ala  Leu  Gly  Thr  Phe  Ser  Arg  Tyr  Glu
65                       70                        75                        80 agt  aca  cgc  agt  ggg  cga  cgg  atg  gag  ctg  agt  atg  ggg  ccc  atc  cag       288
Ser  Thr  Arg  Ser  Gly  Arg  Arg  Met  Glu  Leu  Ser  Met  Gly  Pro  Ile  Gln
                    85                        90                        95 gct  aat  cac  acg  ggc  aca  ggc  ctg  cta  ctg  acc  ctg  cag  cca  gaa  cag       336
Ala  Asn  His  Thr  Gly  Thr  Gly  Leu  Leu  Leu  Thr  Leu  Gln  Pro  Glu  Gln
               100                       105                       110 aag  ttc  cag  aaa  gtg  aag  gga  ttt  gga  ggg  gcc  atg  aca  gat  gct  gct       384
Lys  Phe  Gln  Lys  Val  Lys  Gly  Phe  Gly  Gly  Ala  Met  Thr  Asp  Ala  Ala
          115                       120                       125 gct  ctc  aac  atc  ctt  gcc  ctg  tca  ccc  cct  gcc  caa  aat  ttg  cta  ctt       432
Ala  Leu  Asn  Ile  Leu  Ala  Leu  Ser  Pro  Pro  Ala  Gln  Asn  Leu  Leu  Leu
130                      135                       140 aaa  tcg  tac  ttc  tct  gaa  gaa  gga  atc  gga  tat  aac  atc  atc  cgg  gta       480
Lys  Ser  Tyr  Phe  Ser  Glu  Glu  Gly  Ile  Gly  Tyr  Asn  Ile  Ile  Arg  Val
145                      150                       155                       160 ccc  atg  gcc  agc  tgt  gac  ttc  tcc  atc  cgc  acc  tac  acc  tat  gca  gac       528
Pro  Met  Ala  Ser  Cys  Asp  Phe  Ser  Ile  Arg  Thr  Tyr  Thr  Tyr  Ala  Asp
                    165                       170                       175 acc  cct  gat  gat  ttc  cag  ttg  cac  aac  ttc  agc  ctc  cca  gag  gaa  gat       576
Thr  Pro  Asp  Asp  Phe  Gln  Leu  His  Asn  Phe  Ser  Leu  Pro  Glu  Glu  Asp
               180                       185                       190 acc  aag  ctc  aag  ata  ccc  ctg  att  cac  cga  gcc  ctg  cag  ttg  gcc  cag       624
Thr  Lys  Leu  Lys  Ile  Pro  Leu  Ile  His  Arg  Ala  Leu  Gln  Leu  Ala  Gln
          195                       200                       205 cgt  ccc  gtt  tca  ctc  ctt  gcc  agc  ccc  tgg  aca  tca  ccc  act  tgg  ctc       672
Arg  Pro  Val  Ser  Leu  Leu  Ala  Ser  Pro  Trp  Thr  Ser  Pro  Thr  Trp  Leu
     210                       215                       220 aag  acc  aat  gga  gcg  gtg  aat  ggg  aag  ggg  tca  ctc  aag  gga  cag  ccc       720
Lys  Thr  Asn  Gly  Ala  Val  Asn  Gly  Lys  Gly  Ser  Leu  Lys  Gly  Gln  Pro
225                      230                       235                       240 gga  gac  atc  tac  cac  cag  acc  tgg  gcc  aga  tac  ttt  gtg  aag  ttc  ctg       768
Gly  Asp  Ile  Tyr  His  Gln  Thr  Trp  Ala  Arg  Tyr  Phe  Val  Lys  Phe  Leu
                    245                       250                       255 gat  gcc  tat  gct  gag  cac  aag  tta  cag  ttc  tgg  gca  gtg  aca  gct  gaa       816
Asp  Ala  Tyr  Ala  Glu  His  Lys  Leu  Gln  Phe  Trp  Ala  Val  Thr  Ala  Glu
               260                       265                       270 aat  gag  cct  tct  gct  ggg  ctg  ttg  agt  gga  tac  ccc  ttc  cag  tgc  ctg       864
Asn  Glu  Pro  Ser  Ala  Gly  Leu  Leu  Ser  Gly  Tyr  Pro  Phe  Gln  Cys  Leu
          275                       280                       285 ggc  ttc  acc  cct  gaa  cat  cag  cga  gac  ttc  att  gcc  cgt  gac  cta  ggt       912
Gly  Phe  Thr  Pro  Glu  His  Gln  Arg  Asp  Phe  Ile  Ala  Arg  Asp  Leu  Gly
     290                       295                       300 cct  acc  ctc  gcc  aac  agt  act  cac  cac  aat  gtc  cgc  cta  ctc  atg  ctg       960
Pro  Thr  Leu  Ala  Asn  Ser  Thr  His  His  Asn  Val  Arg  Leu  Leu  Met  Leu
305                      310                       315                       320 gat  gac  caa  cgc  ttg  ctg  ctg  ccc  cac  tgg  gca  aag  gtg  gta  ctg  aca      1008
Asp  Asp  Gln  Arg  Leu  Leu  Leu  Pro  His  Trp  Ala  Lys  Val  Val  Leu  Thr
                    325                       330                       335 gac  cca  gaa  gca  gct  aaa  tat  gtt  cat  ggc  att  gct  gta  cat  tgg  tac      1056
Asp  Pro  Glu  Ala  Ala  Lys  Tyr  Val  His  Gly  Ile  Ala  Val  His  Trp  Tyr
               340                       345                       350 ctg  gac  ttt  ctg  gct  cca  gcc  aaa  gcc  acc  cta  ggg  gag  aca  cac  cgc      1104
```

```
Leu Asp Phe Leu Ala Pro Ala Lys Ala Thr Leu Gly Glu Thr His Arg
            355                 360                 365 ctg ttc ccc aac acc atg ctc ttt gcc tca gag gcc tgt gtg ggc tcc      1152
Leu Phe Pro Asn Thr Met Leu Phe Ala Ser Glu Ala Cys Val Gly Ser
        370                 375                 380 aag ttc tgg gag cag agt gtg cgg cta ggc tcc tgg gat cga ggg atg      1200
Lys Phe Trp Glu Gln Ser Val Arg Leu Gly Ser Trp Asp Arg Gly Met
385                 390                 395                 400 cag tac agc cac agc atc atc acg aac ctc ctg tac cat gtg gtc ggc      1248
Gln Tyr Ser His Ser Ile Ile Thr Asn Leu Leu Tyr His Val Val Gly
                405                 410                 415 tgg acc gac tgg aac ctt gcc ctg aac ccc gaa gga gga ccc aat tgg      1296
Trp Thr Asp Trp Asn Leu Ala Leu Asn Pro Glu Gly Gly Pro Asn Trp
            420                 425                 430 gtg cgt aac ttt gtc gac agt ccc atc att gta gac atc acc aag gac      1344
Val Arg Asn Phe Val Asp Ser Pro Ile Ile Val Asp Ile Thr Lys Asp
        435                 440                 445 acg ttt tac aaa cag ccc atg ttc tac cac ctt ggc cac ttc agc aag      1392
Thr Phe Tyr Lys Gln Pro Met Phe Tyr His Leu Gly His Phe Ser Lys
    450                 455                 460 ttc att cct gag ggc tcc cag aga gtg ggg ctg gtt gcc agt cag aag      1440
Phe Ile Pro Glu Gly Ser Gln Arg Val Gly Leu Val Ala Ser Gln Lys
465                 470                 475                 480 aac gac ctg gac gca gtg gca ctg atg cat ccc gat ggc tct gct gtt      1488
Asn Asp Leu Asp Ala Val Ala Leu Met His Pro Asp Gly Ser Ala Val
                485                 490                 495 gtg gtc gtg cta aac cgc tcc tct aag gat gtg cct ctt acc atc aag      1536
Val Val Val Leu Asn Arg Ser Ser Lys Asp Val Pro Leu Thr Ile Lys
            500                 505                 510 gat cct gct gtg ggc ttc ctg gag aca atc tca cct ggc tac tcc att      1584
Asp Pro Ala Val Gly Phe Leu Glu Thr Ile Ser Pro Gly Tyr Ser Ile
        515                 520                 525 cac acc tac ctg tgg cat cgc cag tga                                  1611
His Thr Tyr Leu Trp His Arg Gln
    530                 535

<210> SEQ ID NO 8
<211> LENGTH: 536
<212> TYPE: PRT
<213> ORGANISM: Homo sapiens

<400> SEQUENCE: 8

Met Glu Phe Ser Ser Pro Ser Arg Glu Glu Cys Pro Lys Pro Leu Asn
1               5                   10                  15

Asp Pro Glu Gly Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
            85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125
```

-continued

```
Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
            195                 200                 205

Arg Pro Val Ser Leu Leu Ala Ser Pro Trp Thr Ser Pro Thr Trp Leu
        210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp His Arg Gln
    530                 535
```

<210> SEQ ID NO 9
<211> LENGTH: 93
<212> TYPE: DNA
<213> ORGANISM: Artificial Sequence
<220> FEATURE:
<223> OTHER INFORMATION: Description of Artificial Sequence: polylinker

<400> SEQUENCE: 9
cggccgcacg cgtgagctcc gcggttcgaa tcccgggatt cgaacatcga taaagatct    60 acgtaggtaa ccacgtgcgg accgagcggc cgc    93

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 10
ggccgggaac ggtgcatt    18

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
gggcaagggg gtgggcctat a    21

<210> SEQ ID NO 12
<211> LENGTH: 77
<212> TYPE: DNA
<213> ORGANISM: Artificial Sequence
<220> FEATURE:
<223> OTHER INFORMATION: Description of Artificial Sequence: polylinker

<400> SEQUENCE: 12
atcgattgaa ttccccgggg atcctctaga gtcgacctgc agaagcttgc tctcgagcag    60
cgctgctcga gagatct    77

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
tccatagaag acaccgggac    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 14
aatccagcct tatcccaacc    20

<210> SEQ ID NO 15
<211> LENGTH: 20
<212> TYPE: DNA

```
<213> ORGANISM: Artificial Sequence
<220> FEATURE:
<223> OTHER INFORMATION: Description of Artificial Sequence: primer

<400> SEQUENCE: 15
tgtccaggac acaagctttg                                                    20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
atgctcatgc atcaggtaag g                                                  21
```

RECOMBINANT ADENO-ASSOCIATED VIRUS VIRIONS FOR THE TREATMENT OF LYSOSOMAL DISORDERS

CROSS-REFERENCE TO RELATED APPLICATION

This application is related to provisional patent application serial No. 60/166,097, filed Nov. 17, 1999 and No. 60/215,430, filed Jun. 30, 2000, from which applications priority is claimed under 35 USC §119(e)(1) and which applications are incorporated herein by reference in their entireties.

FIELD OF THE INVENTION

The present invention relates to recombinant adeno-associated virus (AAV) expression vectors and virions, as well as methods of using the same. More specifically, the present invention relates to recombinant AAV vectors and virions comprising genes encoding proteins deficient or lacking in lysosomal storage diseases, and methods of delivering recombinant AAV virions to a mammalian subject to treat lysosomal storage diseases.

BACKGROUND OF THE INVENTION

Lysosomal storage diseases develop when cells are missing one or more of the many lysosomal enzymes essential for breaking down natural macromolecules. Typically, the undegraded molecules accumulate in the lysosomes to form storage vesicles, which eventually distort cellular structure and compromise function. The result is a chronic and progressive condition that causes a variety of physiological problems often leading to organ failure and premature death. Approximately 40 lysosomal storage diseases have been characterized, each of which involves deficiency in one or more specific enzymes.

A. The Mucopolysaccharidoses (MPS)

The Mucopolysaccharidoses (MPS) include seven subtypes. Each subtype is caused by a defect in an enzyme necessary for the sequential breakdown of glycosaminoglycans. The MPS diseases share many clinical features, although each type may vary in severity. Patients generally suffer from organomegaly, dysostosis multiplex, impaired hearing and vision, cardiovascular abnormalities and joint immobility. MPS I (Hurler's Disease) is caused by a deficiency in α-L-iduronidase necessary to breakdown the glycosaminoglycans, dermatan sulfate and heparin sulfate. MPS II (Hunter's Syndrome) is due to the deficiency of iduronidase-2-sulfatase causing the accumulation of partially degraded heparan and dermatan sulfates. MPS III (Sanfilippo Syndrome) has four subtypes categorized by various deficiencies in sulpaminidase and N-acetylglucosamine 6-sulfatase. MPS IV (Morquoi Syndrome) is due to a deficiency of N-acetylgalactosamine-6-sulphate sulphatase. MPS V (Scheie Syndrome) has a deficiency in a-L-iduronidase that is qualitatively different from MPS I. MPS VI (Maroteaux-Lamy Syndrome) is due to deficiency of N-acetylgalactosamine-4-sulfatase. Finally, MPS VII (Sly Syndrome) is due to a deficiency in the lysosomal enzyme β-glucuronidase (GUS) which aids in the breakdown of glycosaminoglycans (GAGs) (Sly et al. (1973) *J Pediatr* 82: 249–257).

Sly Syndrome is characterized by mental retardation, abnormal bone development, distorted features, and organ malfunctions leading eventually to organ failure (Neufeld et al. (1995) "The mucopolysaccharidoses." In: Scriver C R, Beaudet A L, Sly W S, Valle D (eds), *The Metabolic and Molecular Bases of Inherited Disease.* McGraw-Hill: New York, pp. 2465–2494). Although Sly syndrome is rare, a great deal is known about GUS and because there are animal models of this disease, Sly syndrome has become a paradigm for the study of lysosomal storage diseases in general and for gene therapy in particular.

Both dog (Haskins et al. (1984) *Pediatr Res* 18: 980–984) and mouse (Birkenmeier et al. (1989) *J Clin Invest* 83: 1258–1266) models of MPS VII have been studied. In these models, animals homozygous for mutations eliminating GUS activity display symptoms analogous to those in humans with Sly syndrome. In mice, the mutation is a spontaneous, single base pair deletion that results in a frameshift and a subsequent stop codon in the sequence coding for the GUS protein (Sands et al. (1993) *Proc Natl Acad Sci USA* 90: 6567–6571). Without GUS activity, GAGs cannot be completely catabolized and therefore accumulate in the lysosomes to form storage granules or vacuoles in almost all tissues. This in turn results in animals that have distorted facial features, defects in skeletal development, dwarfism, reduced learning. capacity, and early death at approximately 5 months of age (Birkenmeier et al. (1989) *J Clin Invest* 83: 1258–1266; Bastedo et al. (1994) *J Clin Invest* 94: 1180–1186). Another useful mutation in mice is the "nearly null" GUS mutation, which was developed by V Chapman at Roswell Park Cancer Institute. These mice have only 1–3% of normal GUS activity yet do not display any overt MPS phenotypes. This implies that if a therapy provided even a minimal amount of GUS activity, the progression of MPS pathology would be halted or reversed.

Using the mouse model for MPS VII, several experimental therapies have been tried. These include enzyme replacement (Vogler et al. (1993) *Pediatr Res* 34: 837–840; O'Connor et al. (1998) *J Clin Invest* 101: 1394–1400), a variety of cell transplantation approaches (Bastedo et al. (1994) *J Clin Invest* 94: 1180–1186; Sands et al. (1993) *Lab Invest* 68: 676–686; Poorthuis et al. (1994) *Pediatr Res* 36: 187–193; Moullier et al. (1993) *Nat Genet* 4: 154–159; Naffakh et al. (1994) *J Exp Clin Hematol* 36: S11–S16; Wolfe et al. (1995) *Gene Therapy* 2: 70–78; Taylor et al. (1997) *Nature Med* 3: 771–774), and direct administration of adenoviral vectors (Li et al. (1995) *Proc Natl Acad Sci USA* 92: 7700–7704; Ohashi et al. (1997) *Proc Natl Acad Sci USA* 94: 1287–1292). All of these treatments provided measurable improvement, but none was entirely satisfactory.

Major problems that need to be overcome are the transient nature of enzyme replacement and adenoviral vector therapies, the invasiveness and potential complications of transplantation therapies, and the difficulty in restoring therapeutic GUS activity throughout the organism. The brain in particular has resisted most forms of therapy (Taylor et al. (1997) *Nature Med* 3: 771–774; Sly et al. (1997) *Nature Med* 3: 719–720).

B. Gaucher Disease

Gaucher Disease occurs in approximately 20,000 Americans. Many cases of mild disease are undiagnosed and the actual occurrence of the gene defect in the general population may be as high as 1 in 640.

There are three major types of Gaucher Disease, called Type 1, Type 2 and Type 3. Type 1, an adult-onset form, is the most common form and is non-neuropathic. The disease has a variable spectrum of severity. Clinical manifestations result from macrophages engorged with glucocerebroside which clog and enlarge the liver and spleen and displace normal bone marrow. This results in hepatosplenomegaly, bone pain and fractures, mild anemia and leukopenia, and bleeding due to displacement of platelet precursors in the bone marrow. Pulmonary infiltration by engorged macrophages can cause respiratory failure. Type 2 disease occurs in infants and is characterized by an acute neuropathic phenotype. This subtype has an extensive pathology, including the symptoms of Type 1, as well as oculomotor abnormalities, extreme retroflexion of the neck, limb rigidity, and seizures. Most infants with this form of Gaucher Disease die within the first 2 years of life. Type 3 disease is a juvenile onset form of the disease that presents with mild neurologic involvement in the first decade of life, progressing gradually toward severe neurologic impairment. The severity of Type 3 disease is intermediate to the other subtypes. In addition to the symptoms of Type 1, Type 3 pathology includes massive visceral involvement. CNS manifestations begin with disorders of eye movement, with progression to neurological symptoms equivalent to the severity of Type 2 disease.

A variety of mutations in the glucocerebrosidase (GC) gene cause Gaucher Disease. These gene defects include missense, frameshift and splicing mutations, deletions, gene conversions, and gene fusions with a pseudogene located 16 kb downstream of the GC gene. The most common mutation in Type 1 disease is an A to G transition at nucleotide position 1226 of the GC gene, causing an amino acid substitution which results in the non-neuropathic form of the disease. Neuropathic disease is associated with a T to C transition at nucleotide position 1448 of the GC gene.

Current treatment of Gaucher Disease includes hydration, analgesics and narcotics for pain during bone crises, in addition to the use of Vitamin D, calcium and bisphosphonate. Patients in bone crisis must also be monitored for osteomyelitis, which can be fatal. Joint replacement can be helpful in some patients. Splenectomy can alleviate thrombocytopenia and bleeding episodes, in addition to relieving symptoms due to physical pressure on other organs in the abdominal cavity.

Administration of GC can alleviate some symptoms. Patients receiving GC show improvement in anemia and thrombocytopenia after several months of therapy, followed by regression of organomegaly after about six months of therapy. Bone pain gradually decreases, but X-ray abnormalities persist. Enzyme therapy, however, does not improve CNS symptoms and can cost as much as $200,000 per year per patient. It is therefore cost-prohibitive for some patients. Moreover, the decision to treat a patient with GC is often based on the severity of disease and likely prognosis. Some patients are therefore denied treatment despite likely benefit. Additionally, treatment schedules minimize the effectiveness of enzyme treatment. GC has a half life of approximately 10 minutes and isolated enzyme administration creates a flood of GC during treatment sessions and a lack of GC between treatments. The short half life of GC also limits distribution. In an effort to reduce this bolus effect and decrease the cost of therapy, treatment regimens use less enzyme on a more frequent schedule. This regimen adds further disruption and inconvenience to patients. A continuous supply of GC by a patient's own cells would eliminate enzyme half-life difficulties, remove any bolus effect, enhance distribution, resolve cost issues, and allow Gaucher's patients to lead more normal lives.

C. Other Lysosomal Storage Diseases

Fabry's disease is an X-linked lysosomal storage disease caused by an accumulation of glucosphingolipids in endothelial and perithelial smooth muscle cells. Patients lack α-galactosidase A for cleaving the terminal α-galactosyl of glycosphingolipids. Clinical manifestations of the disease include extremity pain, angiokeratomas of the skin and mucus membranes, corneal opacities, and renal impairment leading to proteinuria, lymphedema, uremia and hypertension. Death occurs from renal failure or heart disease.

Tay-Sachs disease is caused by accumulation of gangliosides in neuronal cells. Patients lack the hexaminidase A subunit necessary for formation of functional hexaminidase heterodimer used to cleave hexose from gangliosides. The ganglioside accumulation in neuronal cells leads to a diffuse apoptotic cell death in the central nervous system. The disease is clinically variable with severe forms showing profound retardation and death by two to three years of age. Late-onset, chronic forms of the disease are dominated by neuronal symptoms such as progressive dystonia, spinocerebellar degeneration, motor neuron disease and psychosis.

Similarly, Sandhoff disease is a deficiency in hexaminidase B, also interfering with formation of functional heterodimeric enzyme. Neurologic symptoms in Sandhoff disease are similar to Tay-Sachs, with additional symptoms related to visceral organ involvement.

Neimann-Pick Disease Types A and B result from accumulation of sphingomyelin due to lack of the lysosomal enzyme acid sphingomyelinase. Type A patients completely lack enzyme activity and, therefore, have more severe disease. Type A clinical pathology begins at 6 months of age with hepatosplenomegaly, lymphadenopathy, anemia and muscular weakness that affects the infants' ability to feed. As macrophages filled with sphingomyelin infiltrate the lungs, bronchitis and pneumonia occur, with respiratory difficulties increasing throughout infancy. Type B patients possess residual enzyme activity, usually about 5 to 10 percent of normal. Clinical presentation is more variable in this form of the disease, with initial symptoms such as hepatosplenomegaly and pulmonary involvement occurring later in infancy or childhood. Type B patients do not typically have neurologic involvement. Type C Neimann-Pick Disease is characterized by accumulation of unesterified cholesterol due to a defect in intracellular trafficking of exogenous cholesterol. This form of the disease also presents with hepatosplenomegaly, progressive ataxia, dystonia, seizures and dementia. These patients present in late childhood and die in the second decade of life. There is currently no treatment for Neimann-Pick Disease.

Several Lysosomal Storage Diseases are caused by enzyme defects necessary for glycoprotein degradation. The glycoproteins are degraded in the lysosome by exoglycosidases, endo-β-N-acetylglycosaminidase and aspartylglucosiminidase. Diseases include Mannosidoses, Fucosidoses, Sialodosis. Symptoms include skeletal deformities, mental retardation and visceromegaly. There is no current treatment for the glycoprotein-related Lysosomal Storage Diseases.

The Mucolipidoses are Lysosomal Storage Diseases characterized by defective transport of enzymes to the lysosome. Mannose-6-phosphate is the receptor ligand necessary for binding and uptake of enzymes into the lysosome. Lack of phospotransferases prevents addition of the mannose-6-phosphate to lysosomal enzymes, preventing the enzyme from entering the lysosome to carry out its function. Affected patients have cellular inclusion bodies filled with storage material and elevated levels of lysosomal enzymes in serum and body fluids. I-cell disease (Mucolipidoses II) and Pseudo-Hurler Polydystrophy (Mucolipidoses III) are the principal disorders. Pathology includes severe psychomotor retardation and premature death.

Acid Lipase Deficiency results in massive accumulation of cholesterol esters and triglycerides in most tissues of the body. There are two major phenotypes, Wolman Disease and Cholesterol Ester Storage Disease. Symptoms can include hepatosplenomegaly, steatorrhea, abdominal distension, gastrointestinal complications, adrenal calcification and extensive atherosclerosis. There is no specific therapy for acid lipase deficiency.

Sulfatide Lipidosis is a lysosomal storage disease caused by accumulation of cerebroside sulfate throughout the nervous system, the kidney and gallbladder. Patients with the disease are deficient in arylsulfatase A which catabolizes cerebroside sulfate in the lysosome. Clinical manifestations include gait disturbance, mental regression and urinary incontinence. As the disease progresses, blindness, loss of speech, quadriparesis, peripheral neuropathy and seizures develop. The two subtypes of the disease are Metachromatic Dystrophy and Multiple Sulfatase Deficiency. The only current treatment for these patients is bone marrow transplantation which merely slows the progression of the disease.

It is readily apparent that alternative and new therapies for the treatment of lysosomal disorders would be highly desirable.

Adeno-associated virus (AAV) provides a means for the delivery of genes to mutant cells. In a number of studies, the lacZ gene delivered by an AAV vector has been shown to make active β-galactosidase in cultured cells and animal tissues (Kaplitt et al. (1994) *Nat Genet* 8: 148–154; Xiao et al. (1996) *J Virol* 70: 8098–8108; Kessler et al. (1996) *Proc Natl Acad Sci USA* 93: 14082–14087; Fisher et al. (1997) *Nature Med* 3: 306–312). In treated muscle of immunocompetent mice, this expression was shown to persist for 1.5 years (Xiao et al. (1996) *J Virol* 70: 8098–8108). Potentially therapeutic proteins that have been delivered and expressed by AAV vectors include erythropoietin (Kessler et al. (1996) *Proc Natl Acad Sci USA* 93: 14082–14087), cystic fibrosis transmembrane conductance regulator (Flotte et al. (1993) *Proc Natl Acad Sci USA* 90: 10613–10617), blood coagulation factor IX (Herzog et al. (1997) *Proc Natl Acad Sci USA* 94: 5804–5809; Monahan et al. (1998) *Gene Therapy* 5: 40–49), and GUS (Fisher et al. (1997) *Nature Med* 3:306–312. In none of these cases, however, were experiments designed to show that the AAV-mediated gene therapy actually affected the long-term course of a disease.

SUMMARY OF THE INVENTION

The present invention is based on the discovery that AAV-mediated delivery of genes encoding enzymes deficient or lacking in lysosomal storage disorders, results in sustained, long-term expression of the gene product in vivo. AAV virions can be administered via the bloodstream, directly to organs, such as the brain or liver, or intrathecally, such as through the spinal column, into cerebrospinal fluid.

In particular, results presented here show that subjects treated with AAV virions encoding β-glucuronidase (QUS), acquire the ability to produce GUS for extended time periods. Furthermore, treatment has a beneficial effect on the subject, as it reduces or eliminates GAG storage in tissues. Morever, intrathecal injection of AAV virions into the cerebrospinal fluid to both neonatal and adult animals, results in therapeutic levels of GUS in the brain and the elimination of storage granules in brain tissue.

Similarly, delivery of AAV virions encoding glucocerebrosidase (GC), via the bloodstream, results in the production of GC in a variety of tissues, such as liver and spleen.

Accordingly, in one embodiment, the subject invention is directed to a method of delivering a recombinant AAV virion to a mammalian subject to treat a lysosomal storage disease. The method comprises:
(a) providing a recombinant AAV virion which comprises a nucleic acid molecule, the nucleic acid molecule comprising a gene encoding a protein defective or missing in the lysosomal storage disease operably linked to control elements capable of directing the in vivo transcription and translation of the gene; and
(b) delivering the recombinant AAV virion to the bloodstream of the subject, whereby the gene is expressed at a level which provides a therapeutic effect in the mammalian subject.

In certain embodiments, the recombinant AAV virion is delivered to the bloodstream by intravenous or intraarterial injection.

In yet further embodiments, the gene is expressed in the liver of the subject.

In another embodiment, the invention is directed to a method of delivering a gene encoding a protein defective or missing in a lysosomal storage disease to a mammalian subject. The method comprises:
(a) providing a recombinant AAV virion which comprises a nucleic acid molecule, the nucleic acid molecule comprising a gene encoding a protein defective or missing in the lysosomal storage disease operably linked to control elements capable of directing the in vivo transcription and translation of the gene; and
(b) delivering the recombinant AAV virion to the liver or brain of the subject, whereby the gene is expressed in the liver or brain at a level which provides a therapeutic effect in the mammalian subject.

In certain embodiments, the recombinant AAV virion is delivered to the brain by intrathecal injection.

In still a further embodiment, the invention is directed to a method of delivering a recombinant AAV virion to a mammalian subject to treat MPS VII. The method comprises:
(a) providing a recombinant AAV virion which comprises a nucleic acid molecule, the nucleic acid molecule comprising a gene encoding β-glucuronidase operably linked to control elements capable of directing the in vivo transcription and translation of the gene; and
(b) delivering the recombinant AAV virion to the subject by intrathecal injection, whereby the gene is expressed at a level which provides a therapeutic effect in the mammalian subject.

In another embodiment, the invention is directed to a recombinant AAV vector comprising a gene encoding β-glucuronidase operably linked to control elements capable of directing the in vivo transcription and translation of the gene in a mammalian cell.

In yet a further embodiment, the invention is directed to a recombinant AAV virion comprising a nucleic acid molecule that comprises a gene encoding β-glucuronidase operably linked to control elements capable of directing the in vivo transcription and translation of the gene in a mammalian cell.

In another embodiment, the invention is directed to a method of producing a recombinant AAV virion. The method comprises:
(a) transfecting a host cell with (i) an AAV vector comprising a gene encoding β-glucuronidase operably linked to control elements capable of directing the in vivo transcription and translation of the gene in a mammalian cell; (ii) AAV helper functions; and (iii) AAV accessory functions, wherein the transfecting is done under conditions that allow the formation of a recombinant AAV virion; and (b) purifying the recombinant AAV virion from the host cell.

These and other advantages of the present invention will become apparent upon reference to the accompanying drawing and upon reading the following detailed description.

BRIEF DESCRIPTION OF THE FIGURES

FIG. 3A shows a normal mouse. FIG. 3B shows an MPS mouse injected with saline via the tail vein; note cytoplasmic vacuolations. FIGS. 3C and 3D show two MPS mice 4 weeks after injection with $10^{12}$ AAV-GUS particles; note normal hepatocellular architecture and absence of cytoplasmic vacuolations (×100 magnification).

FIG. 4A shows the absence of storage vacuoles in an untreated normal mouse. FIG. 4B shows prominent storage vacuoles in an untreated MPS mouse. FIG. 4C shows persistence of vacuoles 20 weeks after intravenous administration of $10^{12}$ AAV-GUS particles to an adult MPS mouse. FIG. 4D shows reduced storage vacuoles 22 weeks after intravenous administration of $10^{12}$ AAV-GUS particles to a newborn MPS-mouse. FIG. 4E shows elimination of vacuoles 6 weeks after intrathecal administration of $5\times10^{11}$ AAV-GUS particles to an adult MPS mouse. FIG. 4F shows the absence of vacuoles 9 weeks after intrathecal administration of $1.5\times10^{11}$ AAV-GUS particles to a newborn MPS mouse. Scale bar, 50 μm.

FIG. 5A shows plasmid pAAV-CMV-hGC, and FIG. 5B shows plasmid pAAV-ApoEHCR/hAAT-hGC, both described in the examples. ITR, AAV inverted terminal repeats; CMV E/P, cytomegalovirus immediate early enhancer and promoter; ApoE/hAAT P, ApoE enhancer/hepatic control region and human alpha 1-antitrypsin promoter; GC, glucocerebrosidase. cDNA; hGH PA, human growth hormone polyadelylation signal.

DETAILED DESCRIPTION OF THE INVENTION

Figure 1A:
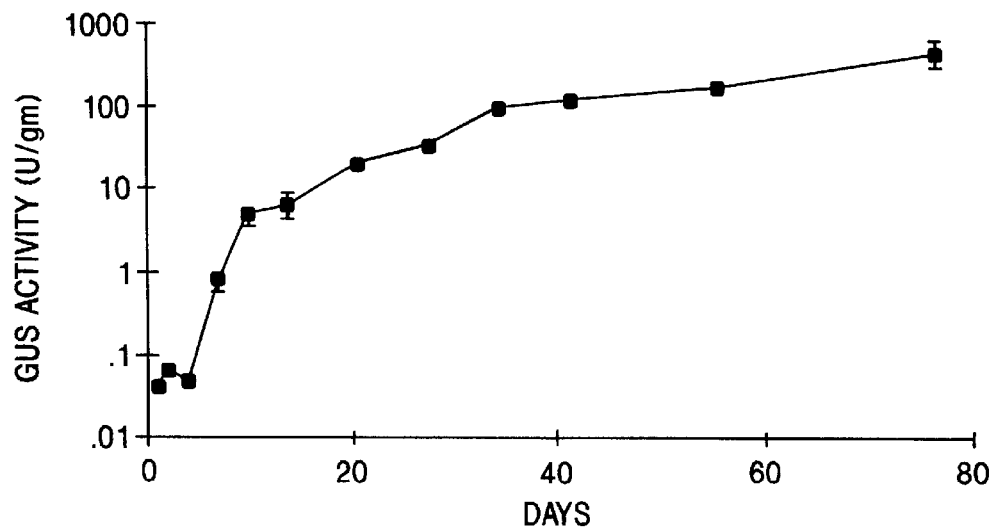
FIGS. 1A and 1B show the time course of GUS expression (FIG. 1A) and vector DNA concentration (FIG. 1B) following intramuscular administration of AAV-GUS virions to NN mice. Each time-point (with bars) represents the mean (±s.e.) of six samples comprised of right and left hind limbs from three animals. AAV-GUS concentration is relative to total (genomic) DNA.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); Freshney *Culture of Animal Cells, A Manual of Basic Technique* (Wiley-Liss, Third Edition); and Ausubel et al. (1991) *Current Protocols in Molecular Biology* (Wiley Interscience, N.Y.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a recombinant AAV virion" includes a mixture of two or more virions, and the like.

I. Definitions

In describing the present invention, the following terms will be employed, and are intended to be defined as indicated below.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), reps and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al., (1989) *J. Virol.* 63:3822–3828; and McCarty et al., (1991) *J. Virol.* 65:2936–2945. A number of other vectors have been described which encode Rep and/or Cap expression products. See, e.g., U.S. Pat. Nos. 6,001,650 and 6,027,931, incorporated by reference herein in their entireties.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, accessory functions can be provided by delivery of helper viruses such as an adenoviruses, a herpesviruses, a cytomegalovirus or a vaccinia virus. Alternatively, elements from these viruses which are involved in AAV replication may be delivered. Adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.), and Muzyczka, N., (1992) *Curr. Topics. Microbiol. and Immun.* 158:97–129. Specifically, early adenoviral gene regions E1A; the E1B 19 kDa protein coding region; the E2A 72 kDa protein coding region; open reading frame 6 (orf 6) or open reading frame 3 (orf 3) of the E4 coding region; and the VA RNA coding region, are thought to participate in the accessory process. See, e.g., U.S. Pat. Nos. 5,945,335 and 6,004,797, incorporated herein by reference in their entireties; and Janik et al., (1981) *Proc. Natl. Acad. Sci. USA* 78:1925–1929. Herpesvirus-derived accessory functions have been described. See, e.g., Young et al., (1979) *Prog. Med. Virol.* 25:113. Vaccinia virus-derived accessory functions have also been described. See, e.g., Carter, B. J. (1990), supra., Schlehofer et al., (1986) *Virology* 152:110–117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

By "capable of supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferably equal to, or greater than, the amount obtained using adenovirus infection.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a nucleotide integration vector and other nucleic acid molecules, into suitable host cells.

The term "transduction" denotes the delivery of a DNA molecule to a recipient cell either in vivo or in vitro, via a replication-defective viral vector, such as via a recombinant AAV virion.

The term "host cell" denotes, for example, microorganisms, yeast cells, insect. cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A promoter "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

By "isolated" when referring to a nucleotide sequence, is meant that the indicated molecule is present in the substantial absence of other biological macromolecules such as other nucleotide sequences, chromatin material, etc. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN, Dayhoff, M. O. (1978) in *Atlas of Protein Sequence and Structure* 5:Suppl. 3, National biomedical Research Foundation, Washington, D.C. Preferably, default parameters are used for alignment. One alignment program is BLAST, used with default parameters. For example, BLASTN and BLASTP can be used using the following default parameters: genetic code=standard; filter=none; strand=both; cutoff=60; expect= 10; Matrix=BLOSUM62; Descriptions=50 sequences; sort by=HIGH SCORE; Databases=non-redundant, GenBank+ EMBL+DDBJ+PDB+GenBank CDS translations+Swiss protein+Spupdate+PIR.

Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. See, e.g., Sambrook et al., supra; *DNA Cloning, supra; Nucleic Acid Hybridization*, supra. For example, stringent hybridization conditions can include 50% formamide, 5×Denhardt's Solution, 5×SSC, 0.1% SDS and 100 μg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2a gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

By "lysosomal storage disease" is meant any disease resulting from the deficiency of one or more lysosomal enzymes necessary for metabolizing natural macromolecules. These diseases typically result in the accumulation of undegraded molecules in the lysosomes, resulting in increased numbers of storage granules (also termed storage vesicles). These diseases are described in more detail below.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

By "therapeutic effect" is meant any therapeutic benefit conferred by the treatment described herein. For example, such an effect can be sustained expression, in an appropriate target tissue, of the enzyme which is deficient or missing in the lysosomal disorder of interest. Additionally, a therapeutic effect may be any reduction or elimination of one or more clinical or subclinical manifestations of the disease of interest. For example, a reduction in the number of storage vesicles (also termed storage granules), or elimination thereof, will provide a therapeutic benefit to the treated subject. Methods for detecting the presence of storage granules in a tissue of interest are well known in the art and described further below in the examples. Such methods entail microscopic examination of tissue sections. See, e.g., Vogler et al. (1990) *Am J Pathol* 136: 207–217. Moreover, reduction in the accumulation of substances due to the particular enzyme deficiency in question, will also confer a therapeutic benefit in the treated subject. Such substances may be readily detected using known assays. For example, MPS VII results in a build-up of undegraded glycosaminoglycans (GAGs). GAG levels can be readily measured using methods developed by Farndale et al. (Farndale et al. (1982) *Con Tissue Res* 9: 247–248) and Poorthuis et al. (Poorthuis et al. (1994) *Pediatr Res* 36: 187–193). See, also, the examples below.

II. General Methods

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

The present invention is directed to novel AAV expression vectors and recombinant virions produced using these vectors, which include genes coding for enzymes defective or missing in lysosomal storage disorders. These recombinant AAV virions are useful in the treatment of a variety of such disorders. The methods described herein provide for long-term, sustained expression of the defective or missing enzyme. Surprisingly, methods described herein allow delivery of a gene of interest to a variety of tissues, including without limitation brain and/or liver. Delivery to desired target tissues may be by any of various methods, described further below, including by administration of recombinant AAV virions to the bloodstream, or by intrathecal, intramuscular and other routes of administration. Moreover, the methods provide for elimination or reduction of storage granules in the treated subject.

Lysosomal storage diseases that may be treated using the methods of the invention include, but are not limited to, Gaucher's disease (see, e.g., Barranger et al. *Neurochemical Res.* (1999) 24:601–615 and *NIH Technology Assessment Conference Statement*, Feb. 27, 1995–Mar. 1, 1995) including Types 1, 2 and 3, Fabry's disease (see, e.g., Takanaka et al. *Exp. Hem.* (1999) 27:1149–1159, Ziegler et al. *Hum. Gene Ther.* (1999) 10:1667–1682 and Takanaka et al. *Hum. Gene Ther.* (1999) 10:1931–1939), Tay-Sachs disease (see, e.g., Guidotti et al. *Hum. Mol. Gen.* (1999) 8:831–838 and Daly et al. *Proc. Natl. Acad. Sci USA* (1999) 96:2296–2300), Neimann-Pick Disease, Types A, B and C, ornithine-δ-aminotransferase (OAT) deficiency (see, e.g., Jensen et al. *Hum. Gene Ther.* (1997) 8:2125–2132, Locrazza et al. *Gene Ther.* (1995) 2:22–28, Rivero et al. *Hum. Gene Ther.* (1994) 5:701–707), hereditary homocysteinemia (see, e.g., McGill et al. *Am. J. Med. Gen.* (1990) 36:45–52, Eikelboom et al. *Ann. Int. Med.* (1999) 131:363–365, Watanabe et al. *PNAS* (1995) 92:1585–1589.), Mannosidoses, Fucosidoses, Sialodosis, the Mucolipidoses, such as I-cell Disease (Mucolipidoses II) and Pseudo-Hurler Polydystrophy (Mucolipidoses III), Acid Lipase Deficiency, such as Wolman Disease and Cholesterol Ester Storage Disease, Sulfatide Lipidosis including Metachromatic Dystrophy and Multiple Sulfatase Deficiency, MPS I (Hurler's disease) (see e.g., Lutzko et al. *Hum. Gene Ther.* (1999) 10:1521–1532, Hartung et al. *Hum. Gene Ther.* (1999) 10:2163–2172), MPS II (Hunter syndrome) (see e.g., Rathmann et. al. *Am. J. Hum. Genet.* (1996) 59:1202–1209, Stronicek et al. *Transfusion* (1999) 39:343–350, Li et al. *J. Med. Genet.* (1999) 36:21–27), MPS III (Sanfilippo syndrome) (see e.g., Scott et al. *Nat. Genet.* (1995) 11:465–467, Jone et al. *J. Neuropath. Exp. Neur.* (1997) 56(10):1158–1167), MPS IV (Morquoi's syndrome) (see e.g., Nothover et al. *J. Inherit. Metab. Dis.* (1996) 19:357–365), MPS V (Scheie's syndrome) (see e.g., Dekaban et al. *Arch. Pathol. Lab. Med.* (1976) 100:231–245), MPS VI (Maroteaux-Lamy syndrome) (see e.g., Hershovitz et al. *J. Inherit. Metab. Dis.* (1999) 22:50–62, Villani et al. *Biochim. Biophys. Acta.* (1999) 1453:185–192, Yogalingam et al. *Biochim. Biophys. Acta.* (1999) 1453:284–296), and MPS VII (Sly syndrome) (see, e.g. Watson et al. *Gene Ther.* (1998) 5:1642–1649, Elliger et al. *Gene Ther.* (1999) 6:1175–1178, Stein et al. *J. Virol.* (1999) 73 (4):3424–3429, Daly et al. *PNAS* (1999) 96:2296–2300, Daly et al. *Hum. Gene Ther.* (1999) 10:85–94); and Sandhoff disease.

The enzymes deficient in the above diseases are known to those of skill in the art. For example, for MPS VII (Sly syndrome), the deficient enzyme is β-glucuronidase (GUS); for Gaucher's disease, the deficient enzyme is glucocerebrosidase (GC); for Fabry's disease, the deficient enzyme is α-galactosidase; for Tay-Sachs disease, the deficient enzyme is the β-hexosaminidase α-subunit; for OAT disease, the defective enzyme is ornithine-δ-aminotransferase; for hereditary homocysteinemia, the defective enzyme can be any of cystathioninemia β-synthase, 5,10-methylenetetrahydrofolate reductase, and methionine synthase; for MPS I (Hurler's disease), the defective enzyme is iduronidase; for MPS II (Hunter's syndrome), the defective enzyme is iduronate-2-sulfatase; for MPS III (Sanfilippo syndrome), the defective enzyme is sulphamidase; for MPS IV (Morquoi's syndrome), the defective enzyme is N-acetylgalactosamine-6-sulphate sulphatase; and for MPS VI (Maroteaux-Lamy syndrome), the defective enzyme is aryl-sulphatase B, for Neimann-Pick Disease the defective enzyme is acid sphingomyelinase, for lysosomal storage diseases caused by defects in glycoprotein degradation such as Mannosidoses, Fucosidoses and Sialodosis, the defective enzymes are exoglycosidases, such as endo-β-N-acetylglycosaminidase and aspartylglucosiminidase, for the Muclolipidoses, the defective enzymes are phosphotransferases, for Sulfatide Lipidosis, the defective enzyme is arylsufatase A, for Sandhoff disease, the defective enzyme is hexosaminidase B.

The invention has been described with particular reference to AAV virions which include genes encoding GUS or GC. The nucleotide sequence and the corresponding amino acid sequence of GUS is well known and described. See, e.g., GenBank Accession No. 4504222 and Oshima et al. (1987) *Proc Natl Acad Sci USA* 84:685–689 (human GUS) and GenBank Accession No. 6754097 and Wawrzyniak et al. (1989) *Mol Cell Biol* 9:4074–4078 (mouse GUS). Additionally, representative nucleotide and amino acid sequences for GUS are depicted in SEQ ID NOS:1–2

(human GUS) and SEQ ID NOS:3–4 (mouse GUS) herein. For human GUS, the mature peptide begins at position 93 of SEQ ID NO:1 (the upstream portion representing a signal peptide). For mouse GUS, the mature peptide begins at position 79 of SEQ ID NO:3 (the upstream portion representing a signal peptide). These sequences, as well as other known GUS sequences, either with or without the sequence encoding the signal peptide, as well as fragments and variants thereof, may be used in the constructs of the present invention, as described further below.

Similarly, the GC sequences are well known. See, e.g., GenBank Accession Nos. M16328 and M11080; and Sorge et al. (1985) *Proc Natl Acad Sci USA* 82:7289–7293, as well as SEQ ID NOS:5–8, herein for the human GC sequences. In particular, the nucleotide sequence for GC includes two potential start codons. See, e.g., *Am J Hum Genet* (1987) 41:1016–1024 and *Biochem J* (1996) 317:81–88. One sequence, depicted in SEQ ID NOS:5–6, encodes a GC protein with 516 amino acids, the first 19 amino acids of which represent a signal peptide. The other sequence, depicted in SEQ ID NOS:7–8, begins with a start codon 60 base pairs upstream of the sequence shown in SEQ ID NO:5 and encodes an amino acid sequence with 536 amino acids, the first 39 amino acids of which represent a signal peptide. Either of these sequences for GC may be used in AAV constructs of the present invention. Moreover, these sequences, as well as other known GC sequences, either with or without the sequence encoding the signal peptide, as well as fragments and variants thereof, may be used in the constructs of the present invention, as described further below.

These genes may be used in their entireties. Alternatively, fragments and variants thereof, that retain the ability to express functional proteins that are deficient or lacking in the lysosomal storage disease of interest, may be used. The term "variant" refers to biologically active derivatives of the reference molecule, or fragments of such derivatives, that retain desired activity, as described above. In general, the term "variant" refers to a molecule, such as a polynucleotide or polypeptide, having a native sequence and structure with one or more additions, substitutions (generally conservative in nature) and/or deletions, relative to the native molecule, so long as the modifications do not destroy enzymatic activity. Preferably, the variant has at least the same biological activity as the parent molecule, and may even display enhanced activity over the parent molecule. Methods for making such variants are well known in the art. For example, the polypeptide produced by the polynucleotide of interest may include up to about 1–70 conservative or non-conservative amino acid substitutions, such as 5–50, 15–25, or any integer between 1–70, so long as the desired function of the molecule remains intact. One of skill in the art may readily determine regions of the molecule of interest that can be modified with a reasonable likelihood of retaining biological activity as defined herein.

By "fragment" is intended a molecule consisting of only a part of the intact, full-length sequence and structure which retains biological activity as described above. The fragment can include a C-terminal deletion and/or an N-terminal deletion of the native polypeptide and will generally include at least about 10–350, such as 25–150 contiguous amino acid residues of the full-length molecule, preferably at least about 50–250 contiguous amino acid residues of the full-length molecule, and most preferably at least about 100–150 or more contiguous amino acid residues of the full-length molecule, or any integer between 10 amino acids and the full-length sequence, provided that the fragment in question retains biological activity as described herein. These examples of fragments, of course, are merely representative and are not meant to be limiting.

Once obtained, the gene of interest is included in an AAV expression vector which is subsequently used to produce recombinant AAV virions which are delivered either directly to the affected subject, or delivered ex vivo, e.g., to cells from the subject, and reintroduced into the subject for the in vivo expression of the defective or missing enzyme. These procedures are described in detail below.

1. AAV Expression Vectors

AAV expression vectors are constructed using known techniques to at least provide as operatively linked components in the direction of transcription, control elements including a transcriptional initiation region, the DNA of interest and a transcriptional termination region. The control elements are selected to be functional in the target mammalian cell or tissue. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable DNA molecules for use in AAV vectors will be less than about 5 kilobases (kb) in size and will include a gene that encodes a protein that is defective or missing from a recipient subject due to a lysosomal storage disease, such as a disease described above. For example, if the targeted disease is MPS VII (Sly syndrome), the gene administered will be that encoding GUS (β-glucuronidase) or a biologically active fragment or variant thereof. If the targeted disease is Gaucher Disease, the gene administered will encode GC (glucocerebrosidase), or a biologically active fragment or variant thereof. Sequences for these genes are described above.

The selected nucleotide sequence is operably linked to control elements that direct the transcription or expression thereof in the subject if the compositions will be delivered in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Other inducible promoters for use in the transcriptional promoter region include the heat shock promoter (hsp); the tetracycline promoter (see, e.g., Bohl et al., (1998) *Blood* 92:1512–1517; Baron et al., (1999) *Proc. Natl. Acad. Sci. USA* 96:1013–1018; Rossi et al., (1998) *Nature Gen.* 20:389–393; Serguera et al., (1999) *Hum. Gene Ther.* 10:375–383); the rapamycin promoter (see, e.g., Ye et al., (1999) *Science* 283:88–91; Rivera et al., (1999) *Proc. Natl. Acad. Sci. USA* 96:8657–8662; Magari et al., (1997) *J. Clin. Inv.* 100:2865–2872; Liberles, et al., (1997) *Proc. Natl. Acad. Sci. USA* 94:7825–7830); and the RU486/mifepristone promoter system (Burcin et al. (1998) *Proc. Natl. Acad. Sci. USA* 96:355–360; Oligino et al., (1998) *Gene Ther.* 5:491–496; Abruzzese et al., (1999) *Hum. Gene Ther.* 10:1499–1507). Tissue-specific promoters, which allow for the gene of interest to be expressed when present in particular target tissues, such as muscle and liver, will also find use herein. Such promoters are well-known in the art.

These promoters need not be present in their entireties, but need only retain those elements necessary for directing transcription of a downstream sequence. In fact, due to the size constraints for packaging AAV vectors, minimal promoter sequences are often desirable. These and other promoter sequences are commercially available from, e.g., Stratagene (San Diego, Calif.) or can be obtained from commercially available plasmids, using techniques well known in the art. See, e.g., Sambrook et al., supra.

One or more enhancer sequences may also be present in the AAV constructs, such as, but not limited to the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1 982b) 79:6777, and elements derived from human CMV, such as elements included in the CMV intron A sequence as described in Boshart et al., *Cell* (1985) 41:521. For example, an intron sequence may also be present, located upstream of the gene of interest, in order to enhance expression thereof. Introns are non-coding regions present in most pre-mRNA transcripts produced in the mammalian cell nucleus. Intron sequences can profoundly enhance gene expression when included in heterologous expression vectors. See, e.g., Buchman et al., *Molec. Cell. Biol.* (1988) 8:4395–4405. Such intron sequences are known and include those derived from, e.g., the human growth hormone sequence, a beta-globin derived intron sequence, a thymidine kinase-derived intron sequence, intron A of the human CMV IE1 enhancer/promoter, and the like.

Transcription terminator/polyadenylation signals may also be present on the various AAV vectors of the invention, located 3' to the translation stop codon for the coding sequence. Such sequences include, but are not limited to, those derived from SV40, as described in Sambrook et al., supra, as well as polyadenylation and termination sequences derived from human and bovine growth hormone. Spacer sequences are optionally present between the polyadenylation sequence and one or both of the flanking ITRs. The spacer length is variable and chosen to ensure that the final packaged vector length is smaller than 5.2 kb, and preferably 4.1 to 4.9 kb.

The AAV expression vectors can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,858,351; 5,962,313; 5,846,528; 5,173,414 and 5,139,941; International Publication Nos. WO 92/01070 (published Jan. 23, 1992) and WO 93/03769 (published Mar. 4, 1993); Lebkowski et al., (1988) *Molec. Cell. Biol.* 8:3988–3996; Vincent et al., (1990) *Vaccines* 90 (Cold Spring Harbor Laboratory Press); Carter (1992) *Current Opinion in Biotechnology* 3:533–539; Muzyczka (1992) *Current Topics in Microbiol. and Immunol.* 158:97–129; Kotin, (1994) *Human Gene Therapy* 5:793–801; Shelling and Smith, (1994) *Gene Therapy* 1:165–169; and Zhou et al., (1994) *J. Exp. Med.* 179:1867–1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 µg/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in the targeted mammalian cell or tissue can be used. The complete chimeric sequence is assembled from overlapping oligonucleotides prepared by standard methods. See, e.g., Edge (1981) *Nature* 292:756; Nambair et al. (1984) *Science* 223:1299; Jay et al. (1984) *J. Biol. Chem.* (1984) 259:6311.

In order to produce rAAV virions, AAV expression vectors are introduced into suitable host cells using known techniques, such as by transfection. A number of transfection techniques are generally known in the art. See, e.g., Graham et al., (1973) *Virology*, 52:456, Sambrook et al., (1989) *Molecular Cloning, a laboratory manual*, Cold Spring Harbor Laboratories, New York, Davis et al., (1986) *Basic Methods in Molecular Biology*, Elsevier, and Chu et al., (1981) *Gene* 13:197. Particularly suitable transfection methods include calcium phosphate co-precipitation (Graham et al., (1973) *Virol.* 52:456–467), direct micro-injection into cultured cells (Capecchi, M. R., (1980) *Cell* 22:479–488), electroporation (Shigekawa et al., (1988) *BioTechniques* 6:742–751), liposome mediated gene transfer (Mannino et al., (1988) *BioTechniques* 6:682–690), lipid-mediated transduction (Felgner et al., (1987) *Proc. Natl. Acad. Sci. USA* 84:7413–7417), and nucleic acid delivery using high-velocity microprojectiles (Klein et al., (1987) *Nature* 327:70–73).

For the purposes of the invention, suitable host cells for producing rAAV virions include microorganisms, yeast cells, insect cells, and mammalian cells, that can be, or have been, used as recipients of a heterologous DNA molecule and that are capable of growth in suspension culture. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

2. AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. Nos. 5,139,941; 6,001,650; and 6,027,931, incorporated herein by reference in their entireties.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the neomycin resistance gene (encoding Aminoglycoside phosphotransferase (APH)) that allows selection in mammalian cells by conferring resistance to G418 (available from Sigma, St. Louis, Mo.). Other suitable markers are known to those of skill in the art.

3. AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter (1990) "Adeno-Associated Virus Helper Functions," in *CRC Handbook of Parvoviruses*, vol. I (P. Tijssen, ed.), and Muzyczka, (1992) *Curr. Topics. Microbiol. and Immun.* 158:97–129.

Specifically, early adenoviral gene regions E1A; the E1B 19 kDa protein coding region; the E2A 72 kDa protein coding region; open reading frame 6 (orf 6) or open reading frame 3 (orf 3) of the E4 coding region; and the VA RNA coding region, are thought to participate in the accessory process. See, e.g., U.S. Pat. Nos. 5,945,335 and 6,004,797, incorporated herein by reference in their entireties; and Janik et al., (1981) *Proc. Natl. Acad. Sci. USA* 78:1925–1929. Herpesvirus-derived accessory functions have been described. See, e.g., Young et al., (1979) *Prog. Med. Virol.* 25:113. Vaccinia virus-derived accessory functions have also been described. See, e.g., Carter, B. J., (1990), supra., Schlehofer et al., (1986) *Virology* 152:110–117.

As a consequence of the infection of the host cell with a helper virus, or transfection of the host cell with an accessory function vector, accessory functions are expressed which transactivate the AAV helper construct to produce AAV Rep and/or Cap proteins. The rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the heterologous nucleotide sequence of interest can then be used for gene delivery, such as in gene therapy applications, to deliver genes to aid in the treatment of lysosomal storage diseases.

4. In vitro and In vivo Delivery of rAAV Virions

Generally, rAAV virions are introduced into the subject using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with the subject's cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, intraarterial, subcutaneous and intraperitoneal injection, or by injection into smooth and cardiac muscle, using e.g., a catheter.

For in vivo delivery, the rAAV virions will be formulated into pharmaceutical compositions and can be administered parenterally in such a way that the systemic circulation is reached. For example, the pharmaceutical compositions may be delivered directly to the bloodstream using intravenous or intraarterial injection, such as into the portal vein or hepatic artery. Alternatively, the rAAV virions may be delivered to a target organ, such as directly to the liver or brain, or by a route that will deliver the rAAV virions to the desired target tissue, such as the liver, e.g., via the portal vein or hepatic artery, or the brain, e.g., by intrathecal delivery to the cerebrospinal fluid space through the spinal cord.

Pharmaceutical compositions will comprise sufficient genetic material to produce a therapeutically effective amount of the protein of interest, i.e., an amount sufficient to reduce or ameliorate symptoms of the disease state in question or an amount sufficient to confer the desired benefit. For example, a reduction in the number of storage vesicles (also termed storage granules), or elimination thereof, will provide a therapeutic benefit to the treated subject. Methods for detecting the presence of storage granules in a tissue of interest are well known in the art and described further below in the examples. Such methods entail microscopic examination of tissue sections. See, e.g., Vogler et al. (1990) *Am J Pathol* 136: 207–217. Moreover, reduction in the accumulation of substances due to the particular enzyme deficiency in question, will also confer a therapeutic benefit in the treated subject. Such substances may be readily detected using known assays. For example, MPS VII results in a build-up of undegraded glycosaminoglycans (GAGs). GAG levels can be readily measured using methods developed by Farndale et al. (Farndale et al. (1982) *Con Tissue Res* 9: 247–248) and Poorthuis et al. (Poorthuis et al. (1994) *Pediatr Res* 36: 187–193). See, also, the examples below.

The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Appropriate doses will depend on the mammal being treated (e.g., human or nonhuman primate or other mammal), age and general condition of the subject to be treated, the severity of the condition being treated, the particular therapeutic protein in question, the mode of administration, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to the bloodstream, as well as intrathecal administration, a therapeutically effective dose will be on the order of from about $10^6$ to $10^{15}$ of the rAAV virions, more preferably $10^8$ to $10^{14}$ rAAV virions. For in vitro transduction, an effective amount of rAAV virions to be delivered to cells will be on the order of $10^8$ to $10^{13}$ of the rAAV virions. The amount of transduced cells in the pharmaceutical compositions will be from about $10^4$ to $10^{10}$ cells, more preferably $10^5$ to $10^8$ cells. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

III. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See, Sambrook et al., supra. Restriction enzymes, $T_4$ DNA ligase, DNA polymerase I, Klenow fragment, and other biological reagents were purchased from commercial suppliers and used according to the manufacturers' directions. Double-stranded DNA fragments were separated on agarose gels.

EXAMPLE 1

IM and IV AAV-GUS Virion Administration for the Treatment of MPS VII

The following examples detail intramuscular and intravenous delivery of AAV virions, which include the gene encoding β-glucuronidase gene (GUS), the enzyme deficient in individuals suffering from MPS VII (Sly Syndrome).

Example 1A

Production of an MPS Animal Model

All procedures using mice were first reviewed and approved by an Institutional Animal Care and Use Committee and adhered to the principles of the NIH 'Guide for the Care and Use of Laboratory Animals.'

$Gus^{mps/+}$ mice in the original C57BL/6 (B6) background were obtained from E. Birkenmeier (Jackson Laboratory, Bar Harbor, Me., USA) and were crossed to the congenic strain B6.Gus$^a$ (Pfister et al. (1982) Biochem Genet 20: 519–535). From the progeny, $Gus^{mps/a}$ mice were selected and were used to establish a breeding colony in which both parents were always $Gus^{mps/a}$ and progeny carried mps/a, a/a or mps/mps allele combinations. The introduction of the a allele was done to aid genotyping by PCR. The homozygous, mps/mps mice are homozygous for the mutant allele, mps, of the β-glucuronidase gene, Gus (Birkenmeier et al. (1989) J Clin Invest 83: 1258–1266), displayed disease symptoms and were essentially identical to the original mutants. Presumably because of reduced viability, homozygous mutant (MPS) mice accounted for about 15–20% of the mice produced, which is somewhat less than the Mendelian expectation.

The am allele of Gus carries an induced mutation identified and provided by V. Chapman (Roswell Park Cancer Institute, Buffalo, N.Y., USA). Because they showed no genetic disease symptoms, these NN (nearly null) mice were bred as homozygotes. NN mice have the genotype $Gus^{am/am}$ and did not display storage disease symptoms in spite of their low levels of GUS enzyme.

GUS activity was measured as follows. Fresh or frozen tissue was homogenized in 0.02 M imidazole (pH 7.4), 0.1% Triton X-100, and assayed for GUS enzyme activity by a fluorometric procedure using 4-methylumbelliferyl-β-glucuronide as the substrate. One unit is the amount of enzyme forming 1 μmol of product per hour at 37° C. Specific activity is given as units per gram (wet weight) of tissue, or units per milligram protein for cultured cells. For per cent normal activity, the activity in a given tissue of a treated animal was compared with the same tissue in normal ($Gus^+/Gus^+$) animals as shown in Table 1 below. A comparison of GUS activities among normal ($Gus^{+/+}$), MPS and NN mice is shown in Table 1. These data suggest that 1–3% of normal GUS activity is sufficient to prevent the accumulation of undegraded GAGs and the resultant disease symptoms.

TABLE 1

GUS activity in normal and mutant mice

| Tissue | Gus activity (U/g tissue) | | | % normal activity | |
|---|---|---|---|---|---|
| | +/+ (n = 5) | NN (n = 5) | MPS (n = 6) | NN | MPS |
| Liver | 36.2 ± 2.3 | 0.12 ± 0.004 | 0.034 ± 0.011 | 0.22 | 0.09 |
| Kidney | 13.9 ± 0.2 | 0.74 ± 0.13 | 0.017 ± 0.004 | 5.3 | 0.12 |
| Spleen | 31.3 ± 1.0 | 0.39 ± 0.022 | 0.005 ± 0.001 | 1.3 | 0.02 |
| Heart | 1.5 ± 0.04 | 0.026 ± 0.006 | 0.005 ± 0.001 | 1.7 | 0.33 |
| Lung | 11.4 ± 0.4 | 0.076 ± 0.009 | 0.014 ± 0.001 | 0.67 | 0.12 |
| Brain | 2.4 ± 0.09 | 0.036 ± 0.004 | 0.007 ± 0.002 | 1.5 | 0.29 |
| Muscle | 1.0 ± 0.04 | 0.022 ± 0.003 | 0.005 ± 0.001 | 2.2 | 0.50 |

Data shown means ± s.e. for n animals. All enzyme assays were done in triplicate. Normal mice were all females and MPS mice were mixed males and females. The enzyme activity in NN kidney is elevated because male NN mice were used and testosterone elevates GUS levels in kidney. Enzyme activities in tissues other than kidney are insensitive to testosterone and do not differ between males and females.

Example 1B

Recombinant AAV-GUS Virion Construction

Vector construction and virion production and purification were analogous to those in previous reports (Kessler et al. (1996) Proc Natl Acad Sci USA 93: 14082–14087; Malik et al. (1997) J Virol (1997) 71: 1776–1783; Matsushita et al. (1998) Gene Ther 5:938–945). AAV-GUS was made by inserting a mouse GUS cDNA sequence (SEQ ID NO:3) into the XhoI site of pV4.1, a plasmid containing a CMV promoter and flanking ITRs. The mouse DNA included 82 bp of genomic DNA 5' to the GUS transcriptional start site, a full-length cDNA coding for the Gus-s$^a$ structural allele, and a piece of polylinker DNA including an XhoI site at the 3' end.

Plasmid pV4.1 was constructed as follows.

A synthetic DNA encoding the restriction enzyme sites NotI-MluI-Ecl136II-SstII-SfuI-SmaI-SfuI-ClaI-BglII-SnaBI-BstEII-PmlI-RsrII-NotI and having the sequence CGGCCGCACGCGTGAGCTCCGCGGTTC-GAATCCCGGGATTCGAACATCGATAAAA-GATCTACGTAGGTAACCACGTGCGGAC-CGAGCGGCCGC (SEQ ID NO:9) was cloned into the blunted KasI and EarI(partial) sites of pUC119 (the vector fragment is 2757 bp in length). A 653 bp SpeI(blunted)-SacII(blunted) fragment encoding the CMV immediate early (IE) promoter, and a 488 bp, SmaI-DraIII fragment containing the human growth hormone polyadenylation site, were cloned into the Ecl136II and SnaBI sites of the aforementioned plasmid, respectively. A chimeric intron composed of the splice donor from the first intron of CMV IE gene and the splice acceptor from the second intron of the human β-globin gene was then installed into the SmaI site of the plasmid in two steps. A DNA fragment encoding the CMV IE gene first intron splice donor was produced by PCR using isolated CMV DNA (strain ad169) as template and the following primers, GGCCGGGAACGGTGCATT (SEQ ID NO:10), and GGGCAAGGGGGTGGGCCTATA (SEQ ID NO:11). This 87 bp fragment was ligated into the SmaI site of the plasmid intermediate. The resulting plasmid was cleaved with BstXI and SmaI, blunted with T4 DNA polymerase, and a 398 bp DraI-EcoRI(blunt) fragment encoding the human β-globin second intron splice acceptor was ligated into the plasmid. The construction of p4.1 was completed by ligation of a polylinker encoding the restriction sites ClaI-EcoRI-SmaI-BamHI-XbaI-SalI-PstI-HinDIII-XhoI-Eco47III-XhoI-BglII between the ClaI and BglII sites of the last intermediate plasmid. The sequence of this synthetic DNA was ATCGATTGAATTCCCCGGG-GATCCTCTAGAGTCGACCTGCAGAAGCT-TGCTCTCGAGCAGCGCTGCTCGAGAGATCT (SEQ ID NO:12).

AAV-GUS virions were produced in an adenovirus-free system by cotransfecting 293 cells with vector DNA, with a plasmid containing the AAV rep and cap genes, and with a plasmid containing adenovirus helper genes (Matsushita et al. (1998) *Gene Ther.*5:938–945). Encapsidated DNA was purified by cesium a chloride gradient centrifugation. Particle titers of greater than $10^{13}$ per milliliter were achieved based on dot blot hybridization. It should be noted that the viable or infective titer may be significantly less than this physical titer.

To test the ability of AAV-GUS to produce GUS enzyme, cultured B lymphocytes derived from a human MPS patient were exposed to the recombinant virions. (The immortalized lymphocyte cell line was provided by I. Olsen, Eastman Dental Institute, University College London.) GUS activity produced was dependent on the dose of AAV-GUS (Table 2), although the multiplicities of infection (MOI) (based on the physical titer) were high. GUS expression diminished with continued culture, suggesting that the majority of transcribed vector was not integrated into the cell genome, but rather was diluted out as cells divided.

TABLE 2

Transduction of MPS cells in culture

| AAV-GUS/Cell | GUS activity (units/mg protein) | |
|---|---|---|
| | 1 week | 2 weeks |
| $2 \times 10^{12}/2 \times 10^6$ | 0.48 ± 0.05 | 0.11 ± 0.01 |
| $2 \times 10^{11}/2 \times 10^6$ | 0.15 ± 0.01 | 0.045 ± 0.006 |
| $0/2 \times 10^6$ | 0.0023 ± 0.0004 | 0.0021 ± 0.0002 |

AAV-GUS was added to cells as indicated. Cells were cultured in 12-well dishes for 1 week and then three wells for each AAV-GUS concentration were harvested for GUS assay. Another three wells of each were washed and cultured in fresh media for another week before being harvested and assayed. Data are means ± s.e. (n = 3).

Example 1C

Intramuscular Administration of AAV-GUS

AAV-GUS virions, produced as described above, were suspended in sterile saline. For intramuscular injections, one or both hind limbs were injected at two distinct sites per limb using 30 µl per injection. In particular, two MPS animals were injected with $2.5 \times 10^{12}$ particles per limb and GUS activity in several tissues was measured 2 weeks later, as described above. As shown in Table 3, GUS expression in injected muscle was exceptionally high while GUS levels in all other tissues tested were low. Lower doses of AAV-GUS ($3.4 \times 10^{11}$ particles per limb) yielded similar, tissue-specific patterns 17 weeks after administration; that is, high expression of GUS was confined exclusively to the injected limbs, which had a mean specific activity of 86±12 U/g (n=6).

TABLE 3

Tissue distribution of GUS after i.m. administration of AAV-GUS

| | Liver | Kidney | Spleen | Heart | Lung | Brain | Muscle (hind leg) |
|---|---|---|---|---|---|---|---|
| U/g | 0.14 | 0.034 | 0.20 | 0.021 | 0.063 | 0.015 | 9.0 |
| % Normal | 0.39 | 0.24 | 0.64 | 1.4 | 0.55 | 0.63 | 900 |

MPS mice were injected at two sites in each hind limb for a total of $2.5 \times 10^{12}$ particles per limb. Mice were 1–2 months old at the time of injection and GUS enzyme activity (Units/g tissue) was assayed 2 weeks after injection. Data are the average of two treated mice.

Because the response to AAV-GUS was high in muscles, NN mice could be used, rather than MPS mice, for additional experiments. The advantage of using NN mice was that they could be bred as homozygotes (unlike MPS mice) and therefore provided more experimental subjects per breeding cage. Also, the overall health of NN mice did not deteriorate at an accelerated pace, as was the case for MPS mice. To look at the dose-response, NN mice were injected as indicated in Table 4. After 2 weeks mice were killed, muscles were dissected from the hind limbs, and GUS enzyme activity was assayed. GUS activity increased with AAV-GUS dose to levels far in excess of normal enzyme levels.

TABLE 4

Dose-response

| Particles injected/leg | GUS (U/g muscle) | % normal activity |
|---|---|---|
| $2.5 \times 10^{12}$ | 21.3 ± 9.9 | 2,130 ± 990 |
| $5 \times 10^{11}$ | 9.6 ± 4.3 | 960 ± 430 |
| $1 \times 10^{11}$ | 2.3 ± 0.6 | 230 ± 60 |
| Saline control | 0.073 ± 0.01 | 7.3 ± 1 |

NN mice were injected at four sites, two in each hind limb, for a total of 60 µl per leg. Mice were killed and enzyme assayed 2 weeks later. Mice were 1 month old at the time of injection. Three mice were injected at each dose. Right and left leg muscles were assayed separately. Data are means ± s.e. (n = 6).

To determine the time-course of AAV-GUS expression, NN mice were injected in the hind limbs using $3.4 \times 10^{11}$ particles AAV-GUS per limb. Three injected NN mice were killed at each time-point. Right and left legs including muscle and bone but not skin, were recovered, homogenized separately, and then assayed for GUS activity as described above. The mean GUS activity levels of injected limbs for each time-point are shown in FIG. 1A. The background level of enzyme activity at 0 days for untreated NN mice was 0.085 U/g tissue. GUS activity at 11 weeks after treatment was more than 200 times the activity in the leg of a normal, non-mutant animal. A single mouse from this experiment was assayed 26 weeks after AAV-GUS administration and had 108 U/g in one leg and 57 U/g in the other, demonstrating that high expression continued for an extended time.

Figure 1B:
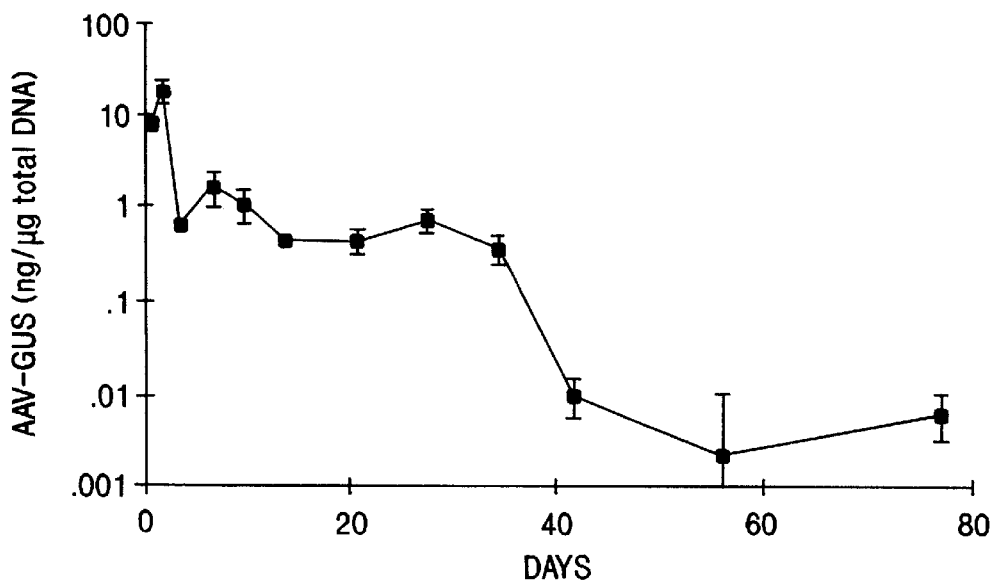

Homogenates used for the time-course shown in FIG. 1A were also used to extract DNA and measure AAV-GUS by quantitative PCR as described below. The mean concentration of vector DNA for each point of the time-course is shown in FIG. 1B. One day after injection, the concentration of vector DNA was 8.5 ng/μg total DNA. After declining rapidly at first, it eventually approached an asymptotic level (7 pg/μg total DNA) that represented about 0.1% of the starting vector DNA. A similar experiment using a lower dose of AAV-GUS confirmed the initial rapid loss of AAV-GUS DNA; compared with the amount of vector DNA 30 min after administration, 34, 16 and 13% remained after 1, 2 and 3 days.

For quantitative PCR, tissue samples for DNA purification were homogenized, digested with proteinase K, and DNA was purified by phenol-chloroform extraction (Sambrook et al. (1989) *Molecular Cloning: A Laboratory Manual*. Cold Spring Harbor Laboratory Press: Cold Spring Harbor, N.Y.). Template concentration standards consisted of purified plasmid DNA containing the AAV-GUS virion diluted in genomic DNA. DNA concentrations were determined by fluorescent staining using Hoechst 33258 (Labarca et al. (1980) *Anal Biochem* 102: 344–352). For the PCR data shown, primers that amplify a section of the vector DNA, but do not amplify any sequences in mouse genomic DNA were used (forward primer, 5'-TCCATAGAAGACACCGGGAC-3' (SEQ ID NO:13); reverse primer, 5'-AATCCAGCCTTATCCCAACC-3' (SEQ ID NO:14; 412 bp PCR product). To confirm results, an alternate set of primers was used, one in exon 4 (forward primer, 5'-TGTCCAGGACACAAGCTTTG-3'; SEQ ID NO:15) and one in exon 5 (reverse primer, 5'-ATGCTCATGCATCAGGTAAGG-3'; SEQ ID NO:16). These amplified both AAV-GUS DNA (289 bp fragment from the cDNA sequence) and genomic GUS DNA (899 bp fragment including intron 4). Thus, the genomic sequence provided an internal control. Both sets of primers gave comparable results.

For PCR reactions, 10 and/or 100 ng samples of DNA from AAV-GUS-treated mice were used. Standards and samples were amplified for 30 cycles at an annealing temperature of 60° C. PCR products were separated electrophoretically on 2% agarosee gels and stained with ethidium bromide. The integrated density values (IDV) of the bands were then calculated using an Alpha Imager (Alpha Innotech, San Leandro, Calif., USA), which digitizes a video input and analyzes the information using computer software. Each set of PCR reactions using DNAs from treated mice was compared with a set of standards run and analyzed simultaneously.

Figure 2:
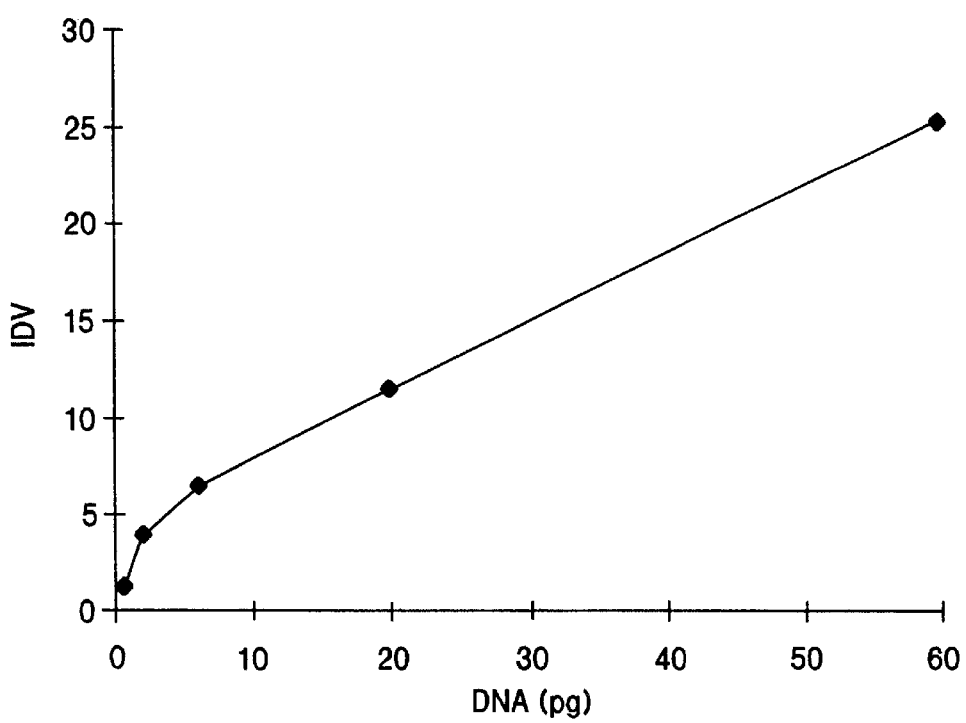
FIG. 2 shows a standard curve for quantitative PCR as described in the examples. Indicated amounts of vector plasmid DNA mixed with 100 ng of vector-free mouse genomic DNA were subjected to PCR as described. Resulting bands on an electrophoretic gel were quantified using an Alpha Imager, which determined an integrated density value (IDV) for each band. IDVs shown are in thousands. IDVs for experimental samples were compared with standards processed in the same PCR run and on the same gel.

A representative standard curve is shown in FIG. 2. As can be seen, under the PCR conditions used, the amount of amplified product was strictly dependent on the amount of vector DNA present. The sensitivity was <0.2 pg of vector DNA in a background of 100 ng of mouse genomic DNA.

Example 1D

Intravenous Administration of AAV-GUS to MPS Mice

MPS mice, 4–6 weeks old, were injected via the tail vein with 200 μl AAV-GUS suspended in saline and GUS activity assessed as described above. Results are shown in Table 5. Compared with intramuscular injection, intravenous injection resulted in a broader tissue distribution of GUS activity. However, of the tested tissues only the liver, heart and muscles had substantially more GUS activity than untreated mutants. This pattern was seen in all animals tested; however, the extent of GUS expression in a given tissue at a given time-point could vary considerably from animal to animal (note SE). This was particularly true for muscle, a tissue that has low normal levels of GUS and in which the vector was expressed with relatively high efficiency. The livers of three animals treated for 13 weeks were also tested for the presence of vector DNA by quantitative PCR. AAV-GUS was present at a concentration of 12±3 pg/μg of total DNA. Other tissues were not tested for the presence of AAV-GUS DNA.

Expression levels of GUS were modest following intravenous injection. To see if there was sufficient enzyme to reduce the stored GAG levels, mice were treated intravenously with $10^{12}$ particles of AAV-GUS and GAG levels were measured after 3 or 8 weeks, by modifying the methods developed by Farndale et al. (Farndale et al. (1982) *Con Tissue Res* 9: 247–248) and Poorthuis et al. (Poorthuis et al. (1994) *Pediatr Res* 36: 187–193). In particular, about 50 mg of tissue was homogenized in 0.5 ml of buffer (50 mM Tris-HCl, pH 7.5, 10 mM $MgCl_2$, 2 mM $Ca_2Cl$), digested with proteinase K for 4 h at 55° C., boiled for 15 min and treated with DNase I (20 U/ml) for 1 h at 37° C. After chloroform extraction, 100 μl of the aqueous phase was passed through a 250 μl Sephadex G-25 spin column. This removed contaminating small molecules that interfere with the dye-binding assay. The flow-through from the spin column was added to 900 μl of dimethylmethylene blue reagent (Farndale et al. (1982) "A direct spectro-photometric microassay for sulfated glycosaminoglycans in cartilage cultures," *Con Tissue Res* 9: 247–248) and the absorbency at 535 nm was measured. Experimental values were compared with chondroitin sulfate C (shark) standards. Protein concentration in the original homogenate was determined using Bio-Rad protein assay mix (Bio-Rad Laboratories, Hercules, Calif., USA), and GAG content was expressed as microgram per milligram protein. The results showed that GAG levels in the liver returned to normal after treatment with vector (Table 6).

TABLE 5

| | MPS mice treated by i.v. injection | | | | | |
|---|---|---|---|---|---|---|
| | GUS activity (units/g tissue) | | | % normal activity | | |
| Tissue | 3 weeks (n = 3) | 8 weeks (n = 3) | 13 weeks (n = 6) | 3 weeks | 8 weeks | 13 weeks |
| Liver | 1.10 ± 0.10 | 3.2 ± 1.1 | 4.9 ± 0.8 | 3.0 | 8.8 | 14 |
| Kidney | 0.021 ± 0.005 | 0.032 ± 0.009 | 0.036 ± 0.016 | 0.15 | 0.23 | 0.26 |
| Spleen | 0.014 ± 0.001 | 0.046 ± 0.011 | 0.065 ± 0.011 | 0.045 | 0.15 | 0.21 |
| Heart | 0.037 ± 0.011 | 0.22 ± 0.02 | 0.25 ± 0.13 | 2.5 | 14 | 17 |

TABLE 5-continued

MPS mice treated by i.v. injection

| Tissue | GUS activity (units/g tissue) | | | % normal activity | | |
|---|---|---|---|---|---|---|
| | 3 weeks (n = 3) | 8 weeks (n = 3) | 13 weeks (n = 6) | 3 weeks | 8 weeks | 13 weeks |
| Lung | 0.013 ± 0.001 | 0.019 ± 0.002 | 0.017 ± 0.001 | 0.11 | 0.17 | 0.15 |
| Brain | 0.004 ± 0.001 | 0.008 ± 0.002 | 0.008 ± 0.003 | 0.17 | 0.33 | 0.33 |
| Muscle | 0.039 ± 0.005 | 1.2 ± 0.8 | 0.053 ± 0.020 | 3.9 | 120 | 5.3 |

Mice were injected via the tail vein with $10^{12}$ AAV-GUS particles in 200 μl saline. After each time-period n mice were killed and GUS activity assayed. Enzyme data are means ± s.e.

TABLE 6

Reduction of GAG levels in liver

| Normal (n = 4) | MPS (n = 4) | MPS + AAV-GUS (3 weeks)(n = 3) | MPS ± AAV-GUS (8 weeks)(n = 3) |
|---|---|---|---|
| 1.31 ± 0.25 | 3.18 ± 0.09 | 1.40 ± 0.05 | 1.05 ± 0.03 |

MPS mice were injected i.v. with $10^{12}$ AAV-GUS particles and were killed 3 or 8 weeks later. GAGs were measured in liver and are expressed as μg GAG/mg protein using a chondroitin sulfate standard. Data are means ± s.e.

Example 1E

Reduction of Storage Vacuoles in AAV-GUS-Treated MPS Mice

One of the most dramatic characteristics of MPS disease is the appearance of large, cytoplasmic, storage vacuoles apparent by microscopic examination of tissue sections (Vogler et al. (1990) Am J Pathol 136: 207–217). MPS mice injected intravenously with either $10^{12}$ AAV-GUS particles or saline alone were sacrificed 4 weeks after administration and examined histologically, as follows. Mice were killed by cervical dislocation and immediately perfused via the left ventricle, first with saline and then with 10% neutral buffered formalin. The fixed animals with exposed viscera were then immersed in formalin before histopathologic evaluation. Selected tissues were routinely processed, embedded in paraffin, cut at approximately 5 microns, stained with hematoxylin and eosin, and examined microscopically.

Figure 3A:
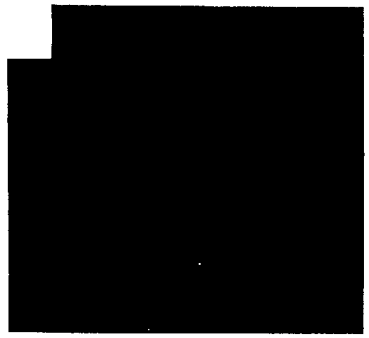
FIGS. 3A–3D show the histopathology of liver from treated and untreated MPS mice.
Figure 3B:
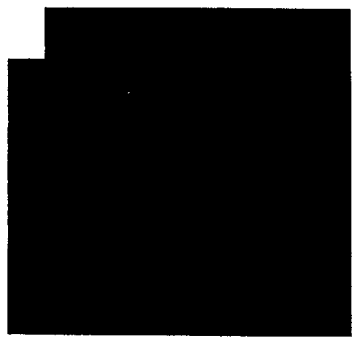
Figure 3C:
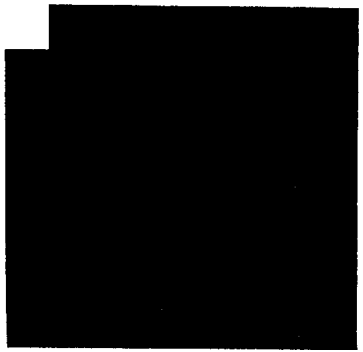
Figure 3D:
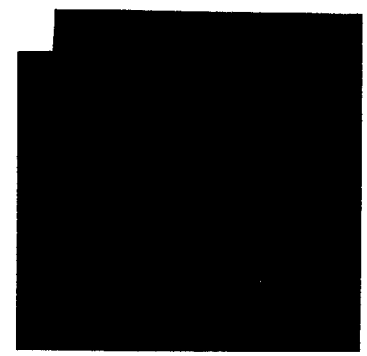

Liver sections from control MPS mice showed moderate to severe, diffuse, cytoplasmic vacuolations in hepatocytes and sinusoidal reticulo-endothelial cells (FIG. 3B). Livers from treated mice had a substantial reduction of storage vacuoles resulting in normal tissue architecture (FIGS. 3C and 3D). This was true for each of three treated MPS mice. Two saline treated and three untreated MPS mice all had extensive storage while normal (FIG. 3A) and NN mice (not shown) did not. Liver sections from MPS mice killed 13 weeks after. AAV-GUS administration were indistinguishable from normal MPS mouse kidney.

EXAMPLE 2

IV and Intrathecal AAV-GUS Virion Administration to MPS Neonatal and Adult Mice

For the experiments presented above, only late juvenile and adult animals were used. Thus, although gene therapy might provide a dramatic improvement in overall health, irreversible damage (e.g., abnormal skeletal development and mental retardation) already has occurred. Ideally, therapy should start as soon as the disease is diagnosed. Accordingly, this example describes experiments treating MPS mice shortly after birth, as well as adult mice using IV and intrathecal modes of administration.

Example 2A

IV Injection of Neonatal Mice with AAV-GUS Virions

Enzyme replacement studies using intravenous injection of GUS enzyme into MPS mice have shown that the brains of neonatal mice are more accessible to the therapeutic protein than the brains of adult mice (Vogler et al. (1993) Pediatr Res 34: 837–840; O'Connor et al. (1998) J Clin Invest 101: 1394–1400). Although this enzyme replacement therapy provided only a temporary source of therapeutic protein, the health and development of mice treated as newborns was markedly improved (O'Connor et al. (1998) J Clin Invest 101: 1394–1400). Therefore, the following experiment was done using newborn MPS mice.

MPS mice were bred and maintained as described in Example 1. AAV-GUS virions were produced as described above. Intravenous injection into neonates was via the superficial temporal vein and consisted of virions suspended in 100 μl saline. The injection mixture also contained 2% non-toxic dye (Schilling green food coloring), in order to monitor the success of the injection procedure.

In particular, newborn MPS VII mice were injected intravenously with AAV-GUS ($10^{12}$ particles per mouse), within the first 3 days postpartum. Mice were sacrificed after 17 to 39 weeks and GUS activity was measured in several tissues (see, Table 7), as described in Example 1.

TABLE 7

Intravenous treatment of neonatal mice

| | 17–22 wks | 37–39 wks | 17–22 wks | 37–39 wks |
|---|---|---|---|---|
| Liver | 1.14 ± 0.43 | 2.0 ± 0.93 | 3.2 | 5.5 |
| Kidney | 0.013 ± 0.002 | 0.049 ± 0.033 | 0.09 | 0.35 |
| Spleen | 0.026 ± 0.003 | 0.043 ± 0.014 | 0.08 | 0.14 |
| Heart | 0.83 ± 0.61 | 2.3 ± 1.5 | 55 | 160 |
| Lung | 0.028 ± 0.013 | 0.040 ± 0.016 | 0.25 | 0.35 |
| Brain | 0.007 ± 0.002 | 0.024 ± 0.016 | 0.29 | 0.99 |
| Muscle | 0.18 ± 0.15 | 0.070 ± 0.056 | 18 | 7.0 |

All mice received a total of $10^{12}$ AAV-GUS particles within the first 3 days postpartum. Data from two mice treated for 17 weeks were averaged with data from one mouse treated for 22 weeks. Similarly, data from one mouse at 37 weeks and two mice at 39 weeks were combined. Data are means ± s.e.

Enzyme activity was elevated most dramatically in liver and heart and only marginally in kidney and brain. This tissue distribution of GUS activity was similar to that seen in adult MPS mice treated by intravenous injection, as described above.

The presence of storage granules in liver and brain was assessed. Storage granules in the liver were examined as described in Example 1. For brain, mice were sacrificed by cervical dislocation, the brain was removed and one hemisphere was fixed in 10% neutral buffered formalin. 5 $\mu$M sections were stained with hematoxylin and eosin (H and E).

Figure 4B:
FIGS. 4A–4F are representations of photomicrographs of cerebral cortex from AAV-GUS-treated and untreated mice.
Figure 4D:
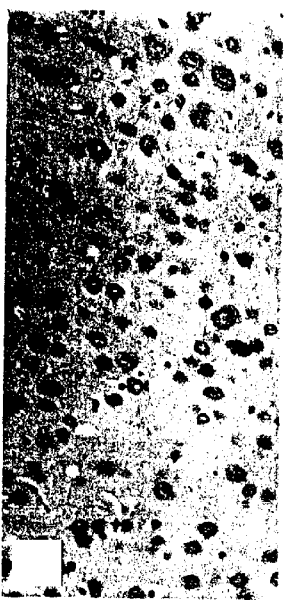
Figure 4F:
Figure 4A:
Figure 4C:
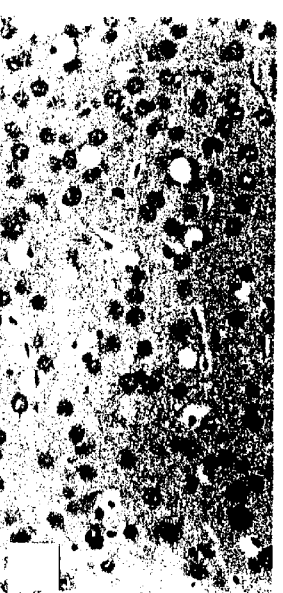

As reported above for adult mice, storage granules in livers of mice treated as newborns were completely eliminated (data not shown). In brain, storage granules were not completely eliminated, but were reduced in size and number after treatment of newborns (FIG. 4D). This partial reduction of stored material in brain was a distinct improvement compared with mice treated as adults (FIG. 4C). Apparently, even the very low levels of GUS in the brain resulting from intravenous treatment of newborns were sufficient for partial improvement.

Example 2B

Intrathecal Injection of Adult and Neonatal Mice with AAV-GUS Virions

In order to determine whether intrathecal administration resulted in improved delivery of AAV-GUS to the brain, the following experiment was performed in neonatal MPS mice.

Three day old neonatal mice were given $1.5\times10^{11}$ particles. Adult mice were 7–13 weeks old at the time of injection and received $5\times10^{11}$ particles. GUS activity in spinal cord was not measured in younger animals. For intrathecal administration to newborns, mice were anesthetized by inhalation of halothane, and virions in 30 $\mu$l saline (with 2% dye) was injected between the sixth lumbar and second sacral vertebrae using a 30-gauge needle. Successful introduction into the cerebrospinal fluid space could be detected immediately as a green streak extending from the spinal column and diffusing into the brain. For intrathecal administration to adults, MPS mice were anesthetized with avertin (tribromoethanol) and a 1 cm incision was made through the skin parallel to the spine to make the positions of individual vertebrae visible. Virions in 100 $\mu$l saline (with 2% dye) were injected between the last thoracic and second lumbar vertebrae.

At increasing times after this treatment, mice were sacrificed and tissues were analyzed for GUS levels as described above. Therapeutic levels of GUS enzyme were observed in brain for every animal treated (Table 8) and histopathology indicated that brain tissue from these treated mice was completely free of storage vacuoles (FIG. 4F). In these studies, it was difficult to determine whether the kinetics of expression was the same as in muscle.

Figure 4E:

Although early treatment is clearly desirable, MPS diseases in humans are not usually detected until some damage has already appeared and lysosomal storage is already significant. Thus, we tested whether we could successfully treat adult MPS mice in which storage granules had already developed and in which the brain had already been shown to be less accessible to AAV-GUS introduced intravenously. Intrathecal administration of AAV-GUS to adult MPS mice did result in significant GUS enzyme activity in the brain (Table 8, last line). This was accompanied by the elimination of storage vacuoles in the brain (FIG. 4E), suggesting that previous constraints to successful treatment had been overcome.

TABLE 8

| | | Intrathecal administration of AAV-GUS | | | | |
|---|---|---|---|---|---|---|
| MPS mice | Weeks after | GUS activity (% normal) | | | | |
| treated | treatment | Brain | Spinal Cord | Liver | Heart | Muscle |
| 3 Neonates | 1 | 10 ± 4.8 | ND | 2.5 ± 2.2 | 3.0 ± 2.3 | 5.0 ± 3.0 |
| 2 Neonates | 2 | 3.1 ± 1.3 | ND | 0.11 ± 0 | 0.44 ± 0.04 | 0.7 ± 0.10 |
| 2 Neonates | 3 | 5.0 ± 2.3 | ND | 0.14 ± 0.07 | 0.47 ± 0 | 0.6 ± 0.10 |
| 2 Neonates | 4 | 8.5 ± 3.5 | 21 ± 10 | 0.42 ± 0.02 | 0.84 ± 0.04 | 0.75 ± 0.05 |
| 3 Neonates | 6 | 31 ± 24 | 660 ± 250 | 2.2 ± 0.8 | 1.7 ± 0.8 | 0.40 ± 0.06 |
| 2 Neonates | 9 | 16 ± 2.5 | 650 ± 80 | 1.4 ± 0.8 | 1.4 ± 0.4 | 1.2 ± 0.4 |
| 3 Neonates | 13 | 25 ± 19 | 320 ± 120 | 4.2 ± 3.4 | 0.78 ± 0.15 | 0.57 ± 0.15 |
| 5 Adults | 6 | 7.8 ± 3.2 | 1700 ± 1400 | 4.2 ± 1.9 | 3.4 ± 2.1 | 1.1 ± 0.5 |

Data are means ± s.e. ND, not determined.

Brain samples from mice treated as adults were also tested for the presence of vector DNA using the quantitative PCR method described above. Vector DNA levels were 0.65±0.23 pg vector DNA per $\mu$g total (genomic) DNA at 6 weeks after treatment by intrathecal injection. This was equivalent to an average of about 0.8 copies of the vector per diploid nucleus, suggesting that some, but not all, brain cells had the capacity to make GUS. This implies that some brain cells benefit from a bystander effect, which is consistent with observations that GUS can be transferred between cells that are in close proximity in the brain (Taylor et al. (1997) Nature Med 3: 771–774).

As shown above, the administration of a recombinant viral vector, AAV-GUS via intrathecal injection into the cerebrospinal fluid, resulted in significant GUS enzyme activity in the brain. Intrathecal treatment of either newborn or adult mutant mice resulted in long-term elimination of storage granules in brain tissue.

The results presented in Examples 1 and 2 show that this type of treatment provides relief from the mental deterioration that accompanies many of the lysosomal storage diseases in humans.

EXAMPLE 3

Use of Recombinant AAV Virions for the Treatment of Gaucher Disease

Gaucher disease is a lysosomal storage disease that results from mutations in the glucocerebrosidase (GC) gene. In order to test the ability of recombinant AAV virions to treat Gaucher Disease, the following experiments were conducted.

Example 3A

Production of Recombinant AAV Virions Including the GC Gene

Two recombinant AAV vectors, containing the GC gene, were constructed to test the feasibility of using AAV to treat Gaucher disease. One vector utilized a CMV enhancer/promoter for expression in muscle tissue and the other used an hepatic-specific promoter for expression in liver tissue.

Figure 5A:
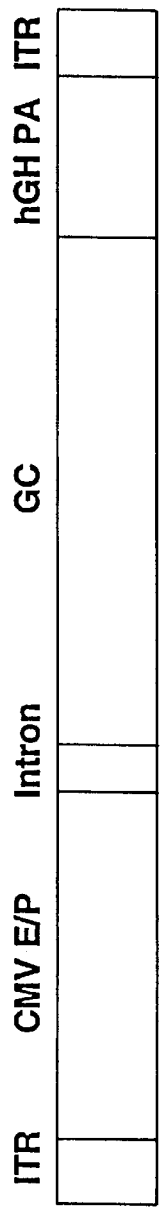
FIGS. 5A and 5B are schematic diagrams of recombinant AAV glucocerebrosidase (GC) expression vectors.

As explained above, the human GC cDNA contains two potential ATG start codons which result in two signal peptides of different hydrophobicities. One signal peptide is 39 amino acids in length, while the other is 19 amino acids. It has been demonstrated that either ATG can function to produce active GC in cultured cells (Sorge et al. (1987) *Am J Hum Genet* 41:1016–1024). The two expression cassettes that were constructed utilized the different initiation codons. These two vectors were tested in vitro for their ability to express biologically active GC of the predicted molecular weight, as described further below In particular, plasmid pAAV-CMV-hGC was made by inserting a human GC cDNA (either the sequence of SEQ ID NO:5 or the sequence of SEQ ID NO:7) between the ClaI and BglII site of pV4.1. Plasmid pV4.1 is described above in Example 1. The expression cassette in the plasmid pAAV-CMV-hGC contains the CMV immediate early enhancer and promoter, a chimeric intron consisting of a CMV splice donor sequence and a β-globin splice acceptor sequence, a 1545 bp fragment of the human GC cDNA containing the 19 amino acid signal sequence, and a human growth hormone polyadenylation sequence. This expression cassette was flanked between two AAV inverted terminal repeats. See, FIG. 5A.

Figure 5B:
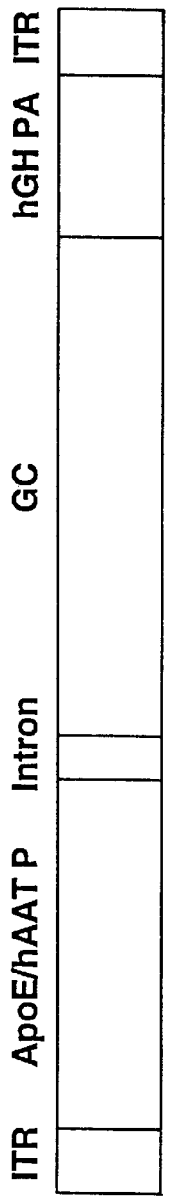

The other plasmid, pAAV-ApoEHCR/hAAT-hGC (FIG. 5B), contained a similar expression cassette, except the CMV enhancer/promoter was replaced by the ApoE enhancer/hepatic control region (HCR) and a human alpha 1-antitrypsin (hAAT) promoter (both described in Miao et al. (2000) *Molec Ther* 1:432), and contained a 1605 bp fragment of hGC cDNA utilizing the 39 amino acid signal sequence. The corresponding recombinant virions were produced essentially as described above in Example 1, using the triple transfection method (Matsushita et al. (1998) *Gene Ther* 5:938–945) and were purified by heparin affinity column chromatography. Vector genomes were quantified using a quantitative dot-blot assay.

Example 3B

In Vitro Transduction of Cell Lines with Recombinant AAV-GC Virions

Human embryonic kidney 293 (HEK 293) cells (American Type Culture Collection, Manassas, Va.) or HepG2 cells were seeded in six-well plates at a density of $8\times10^5$ cells per well. After 24 hours, the 293 cells were infected with AAV-CMV-hGC recombinant virions and the HepG2 cells were infected with AAV-ApoEHCR/hAAT-hGC recombinant virions at MOIs of $1\times10^4$ or $1\times10^5$. 24 hours post-infection, the media was replaced with DME/10% heat-inactivated fetal bovine serum (FBS) and was collected 48 hours later for analysis. Culture supernatants and cell lysates were analyzed for GC activity as follows.

The GC assay was performed on cell culture supernatants and cell lysates according to the procedure described by Liu et al. (1998) *J Mol Med* 76:773–781. Cell lysates were harvested and stored frozen until analysis. Cell pellets were resuspended in cold lysis buffer (potassium phosphate buffer (PBS), pH 6.5; 1% Triton X-100) followed by ultrasonification for 10 seconds. The lysates were incubated for 1 hour at 4° C. and were subsequently centrifuged (20,000 g) at 4° C. for 15 minutes and the supernatants were collected. The protein concentration in the cell extracts was determined using a Bradford kit (Bio-Rad, Richmond, Calif.). GC activity present in the cell extracts or culture medium was measured by incubating the sample with 5 mM 4-methylumbellifery-glucopyranoside (4-MUG) (Sigma, St. Louis, Mo.) in 0.12 M citric acid-sodium phosphate (pH 5.2), 0.25% sodium taurocholate, 0.25% Triton X-100, at 37° C. for one hour. The reaction was stopped by the addition of 0.1 M glycine-NaOH, pH 10. The product of the enzymatic reaction, 4-methylumbelliferone (4-MU), was measured with a Molecular Devices Luminescence Spectrometer (excitation wavelength 340 nm, emission wavelength 448 nm) and was quantified against a standard curve generated with the 4-MU product (Sigma, St. Louis, Mo.). GC activity is expressed in nanomoles per hour per milligram of protein or nanomoles per hour milliliter of culture supernatant.

Figure 6:
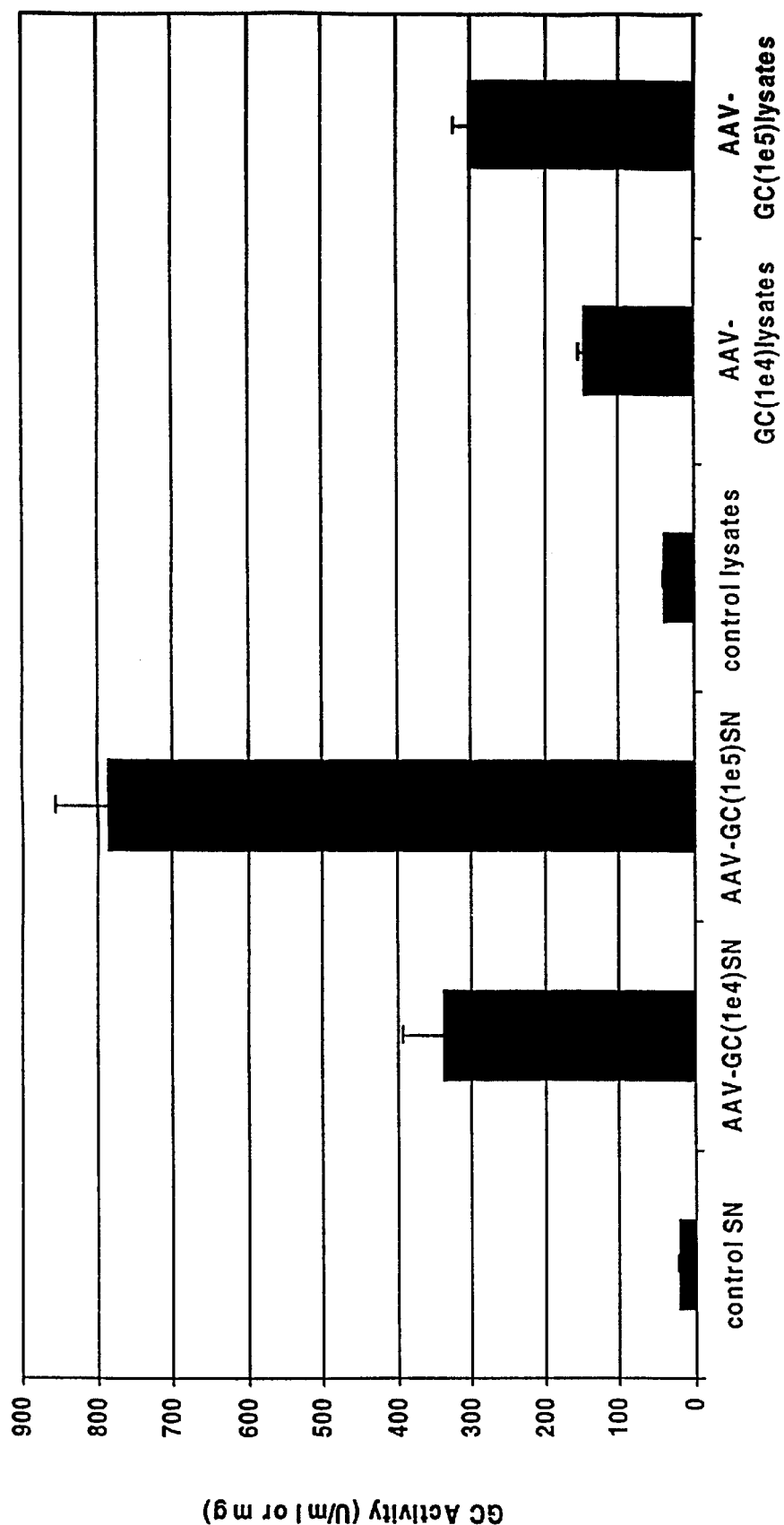
FIG. 6 shows GC activity in supernatants (SN) and lysates of control 293 cells, or 293 cells transduced with AAV-CMV-hGC at an MOI of $1\times10^4$ or $1\times10^5$ vector genomes per cell.

As shown in FIG. 6, 293 cells transduced with AAV-CMV-hGC recombinant virions secreted high levels of GC activity. When an MOI of $1\times10^4$ was used, average GC levels of 338 U/ml were observed in the media, which is 16-fold above the background levels observed in non-transduced cells. At a ten-fold higher MOI, GC activity levels of 785 U/ml were seen, demonstrating a dose response to the vector.

Figure 7:
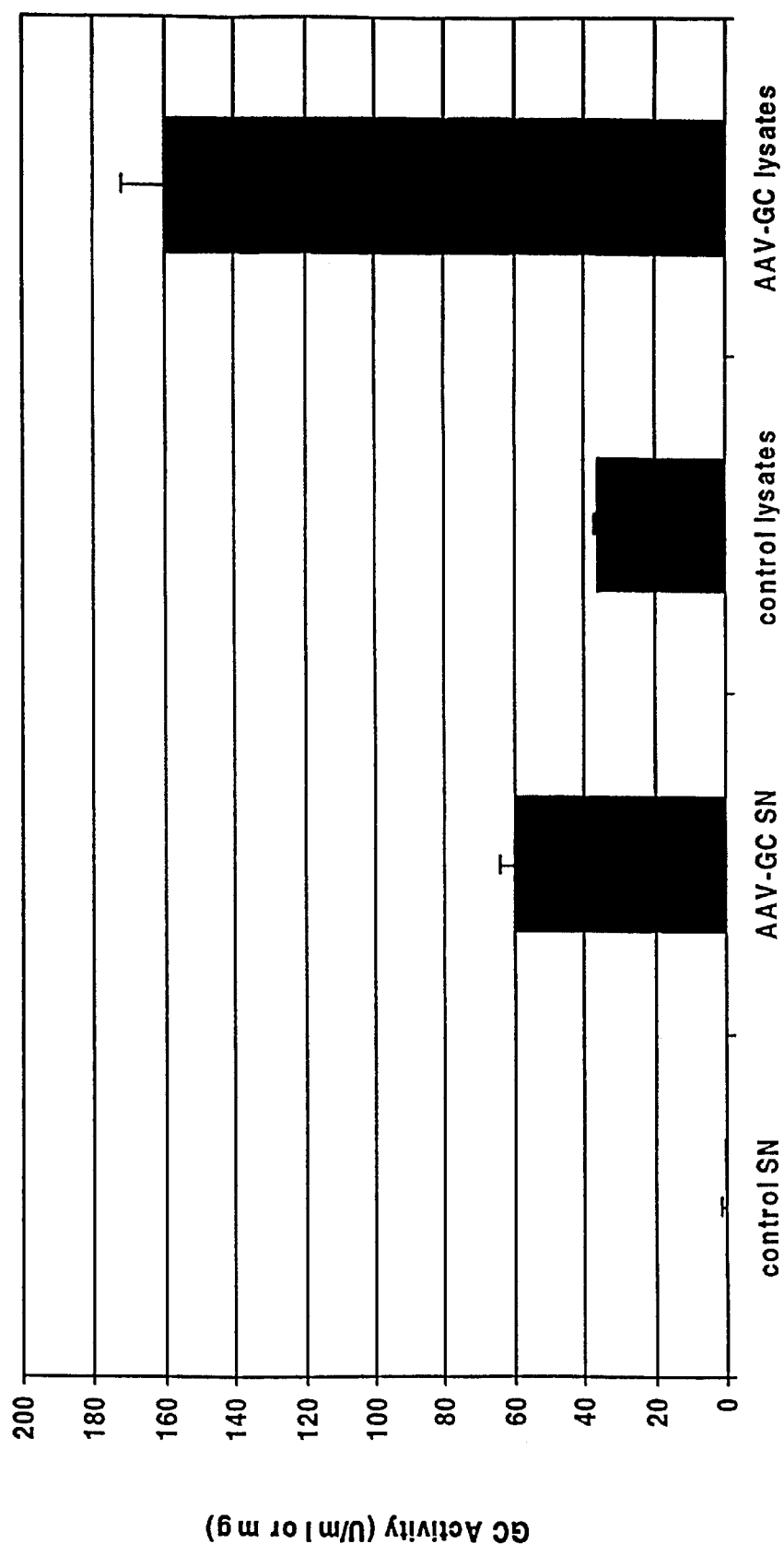
FIG. 7 shows GC activity in supernatants (SN) and lysates of control HepG2 cells or HepG2 cells transduced with AAV-ApoEHCR/hAAT-hGC at an MOI of $1\times10^5$ vector genomes per cell.

Supernatants from AAV-ApoEHCR/hAAT-hGC-transduced HepG2 cells had lower but detectable GC activity (FIG. 7). At an MOI of $1\times10^5$, average GC levels of 64 U/ml, were observed. Intracellular GC activity in the cell extracts was also determined, and significant activity levels over background were observed in both transduced 293 and HepG2 cells (FIGS. 6 and 7). These data demonstrate that both the AAV-CMV-hGC and AAV-ApoEHCR/hAAT-GC recombinant virions are able to transduce cells in culture and express biologically active GC.

Figure 8:
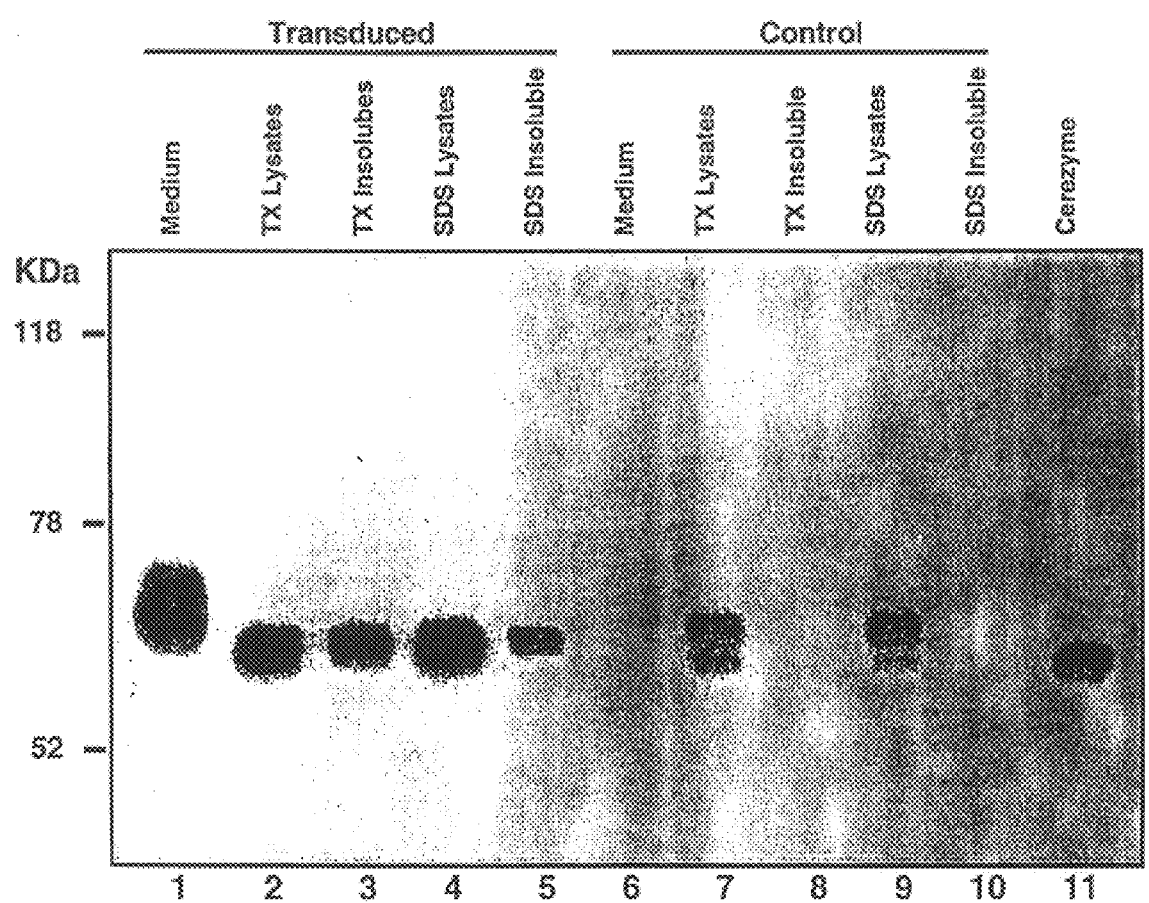
FIG. 8 depicts the results of Western blot analysis of GC expression in 293 cells. Lanes 1–5 represent samples from AAV-CMV-hGC-transduced cells and lanes 6–10 represent samples from nontransduced control cells. Cells were extracted with either Triton X100 (TX) or Triton X100 and SDS (SDS). Samples were loaded on SDS-PAGE, transferred onto nitrocellulose, blotted by anti-human GC monoclonal antibody 8E4 and detected by ECL detection kit (Amersham Pharmacia Biotech, Piscataway, N.J.).
Figure 9:
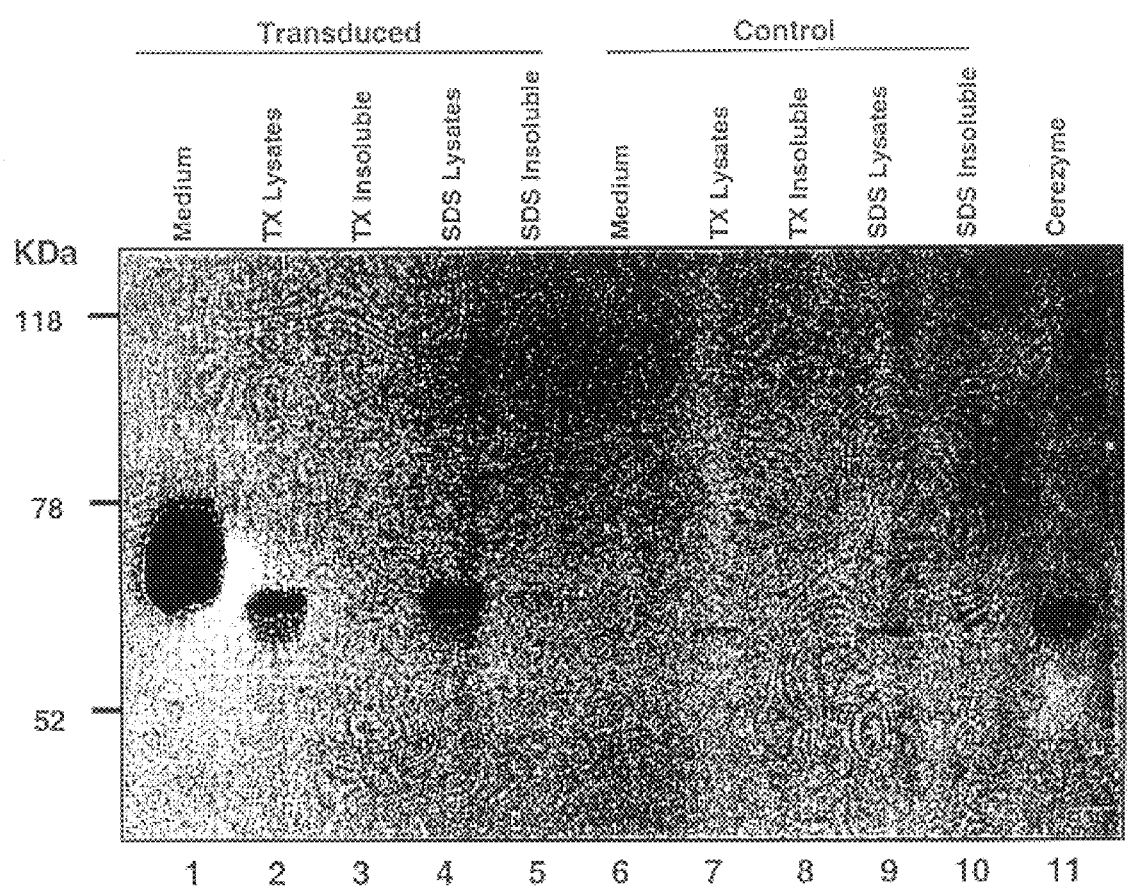
FIG. 9 shows the results of Western blot analysis of GC expression in HepG2 cells. Lanes 1–5 represent samples from AAV-ApoEHCR/hAAT-hGC-transduced cells and lanes 6–10 represent samples from nontransduced control cells. Cells were extracted with either Triton X100 (TX) or Triton X100 and SDS (SDS). Samples were loaded on SDS-PAGE, transferred onto nitrocellulose, blotted by anti-human GC monoclonal antibody 8E4 and detected by ECL detection kit (Amersham Pharmacia Biotech, Piscataway, N.J.).

Western blot analysis was also performed to determine the size of the expressed GC protein. Cell extracts or cell culture supernatants were separated by SDS-PAGE and transferred to nitrocellulose. Western blotting with the anti-human GC monoclonal antibody 8E4 (gift of J. Aerts, E. C. Slater Institute, Amsterdam, The Netherlands) revealed that culture supernatants of both transduced 293 (FIG. 8, lane 1) and HepG2 (FIG. 9, lane 1) contained a 65 kDa protein band, which was absent in nontransduced cell culture supernatants (FIGS. 8 and 9, lane 6, respectively). This suggests that the GC that was secreted from the transduced cells was in a glycosylated form.

Cells were extracted with Triton X100 and with or without SDS to determine whether the combination of detergents would improve the solubility of GC from the cells. As shown in FIGS. 8 and 9, GC-cross reactive bands with molecular weights ranging from 60 kDa to 65 kDa, were seen in both the soluble and insoluble fractions of the extracted cells (FIGS. 8 and 9, lanes 2–5 and lanes 7–10). More GC was solubilized from 293 cells when both detergents were used; however, addition of SDS did not release more GC from the HepG2 cells. Two bands of different intensity were also observed in the nontransduced cells, which represent the endogenous hGC protein. The different molecular weight species of GC bands observed presumably represents different degrees of glycosylation of the protein.

Cerezyme (remodeled recombinant GC) was loaded on the gel as a positive control (FIGS. 8 and 9, lane 11). As expected, a band of 60 kDa was observed which corresponded to the re-modeled protein, devoid of complex oligosaccharides. The combined results indicated that biologically active GC of the correct size was expressed from both the AAV-CMV-hGC and AAV-ApoEHCR/hAAT-hGC vectors in vitro.

Example 3C

In Vivo Expression of GC Following Plasmid Injection of GC Constructs

In order to test the potency of the GC expression cassettes in vivo, plasmid DNA was injected into the tail veins of C57B1/6 mice using the procedure described by Budker et al (Budker et al. (1998) *Gene Ther* 5:272–276). Serum, liver, and spleen tissues were analyzed for GC activity.

In particular, C57B1/6 mice (Jackson Laboratories, Bar Harbor, Me.) were rapidly injected via the tail vein with 40 μg of pAAV-CMV-hGC or pAAV-ApoEHCR/hAAT-hGC in 2 ml of PBS in 5 seconds. A control group of animals was injected with PBS. Serum samples were collected via the retroorbital plexus 24 hours post-injection and analyzed for GC activity. In addition, liver and spleen were harvested, snap frozen, and stored at −80° C. until use. Tissue extracts were prepared by mincing 100 mg of liver and spleen tissue, diluting the tissue 1:5 (wt/vol) in cold PBS (pH 6.5) containing 1% Triton X-100, and homogenizing with a motor-driven tissue grinder (VWR, Willard, Ohio). After a 1 hour incubation at 4° C., the suspensions were centrifuged (20,000 g) at 4° C. for 15 minutes, and the supernatants were collected. The soluble protein concentration in the supernatants was determined using the Bio-Rad Bradford kit. GC activity was determined as described above.

Figure 10:
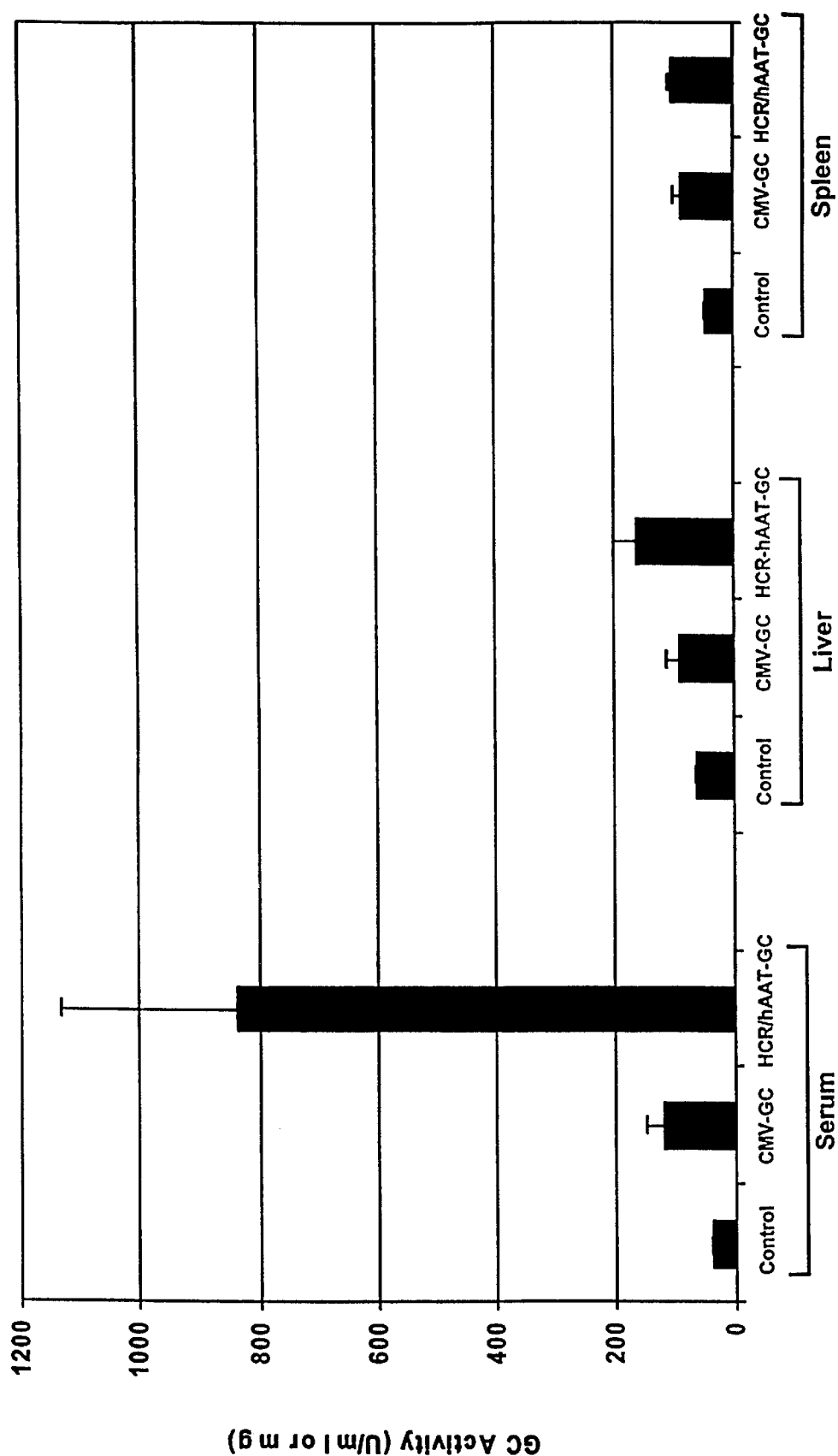
FIG. 10 shows GC expression in serum, liver and spleen of plasmid-injected mice. Control: serum or tissues from uninjected mice (n=2). CMV-GC: serum or tissues from AAV-CMV-hGC plasmid injected mice (n=3). HCR/hAAT-GC: serum or tissues from AAV-ApoEHCR/hAAT-hGC plasmid injected mice (n=3).

As shown in FIG. 10, 24 hours after injection of plasmid DNA, GC activity was detected in the serum, liver and spleen. Extremely high levels of GC activity (ave. 838 U/ml) were detected in the serum of animals injected with plasmid pAAV-ApoEHCR/hAAT-hGC, which was 20-fold higher than the GC activities observed in the PBS controls. An approximately three-fold increase in GC activity over background was observed in the liver and a two-fold increase was seen in the spleen of these animals. The average GC activity in the serum from pAAV-CMV-hGC-injected mice was approximately 118 U/ml. Livers and spleens from these animals had GC activities that were twice the level seen in the controls. Western blot analysis confirmed that plasmid-injected mice expressed human GC of the correct the size in these tissues (data not shown). These date indicate that the GC expression cassettes direct expression of biologically active GC in vivo, and the plasmid containing the liver specific promoter (pAAV-ApoEHCR/hAAT-hGC) was extremely efficient at expressing and secreting high levels of the active protein.

Example 3D

In Vivo Expression of GC Following Recombinant AAV-GC Virion Injection

An animal experiment was designed to assess the expression of human GC in mouse tissues following intramuscular and portal vein administration of the recombinant AAV-CMV-hGC and AAV-ApoEHCR/hAAT-hGC virions, respectively. Expression was assessed by measuring GC activity in plasma and tissue.

In particular, 50 immunodeficient B6;129-Rag1 mice were injected intramuscularly with $3\times10^{11}$ particles of AAV-CMV-hGC or PBS/Sorbitol. Plasma was drawn from animals at 2-week intervals for the first month and at monthly intervals subsequently. A cohort of 4 vector-treated and 4 PBS/Sorbitol-treated animals was sacrificed 4, 8, 16, and 24 weeks post-injection, and liver and spleen were harvested and processed for GC analysis as described above. Frozen liver and spleen sections were also prepared for immunostaining using the human GC-specific antibody 8E4.

In a separate experiment, 49 mice were injected via the portal vein with $3\ 10^{11}$ vector genomes of AAV-ApoEHCR/hAAT-hGC. The collection of plasma and tissue samples was identical to that described above.

A control group (n=4) of animals was also injected with Cerezyme (remodeled recombinant GC) at a dose of 60 U/kg. Two animals were sacrificed 10 min post-injection and two animals were sacrificed 1 hour following the injection. Plasma, liver and spleen samples were collected at both time points for GC analysis.

Figure 11:
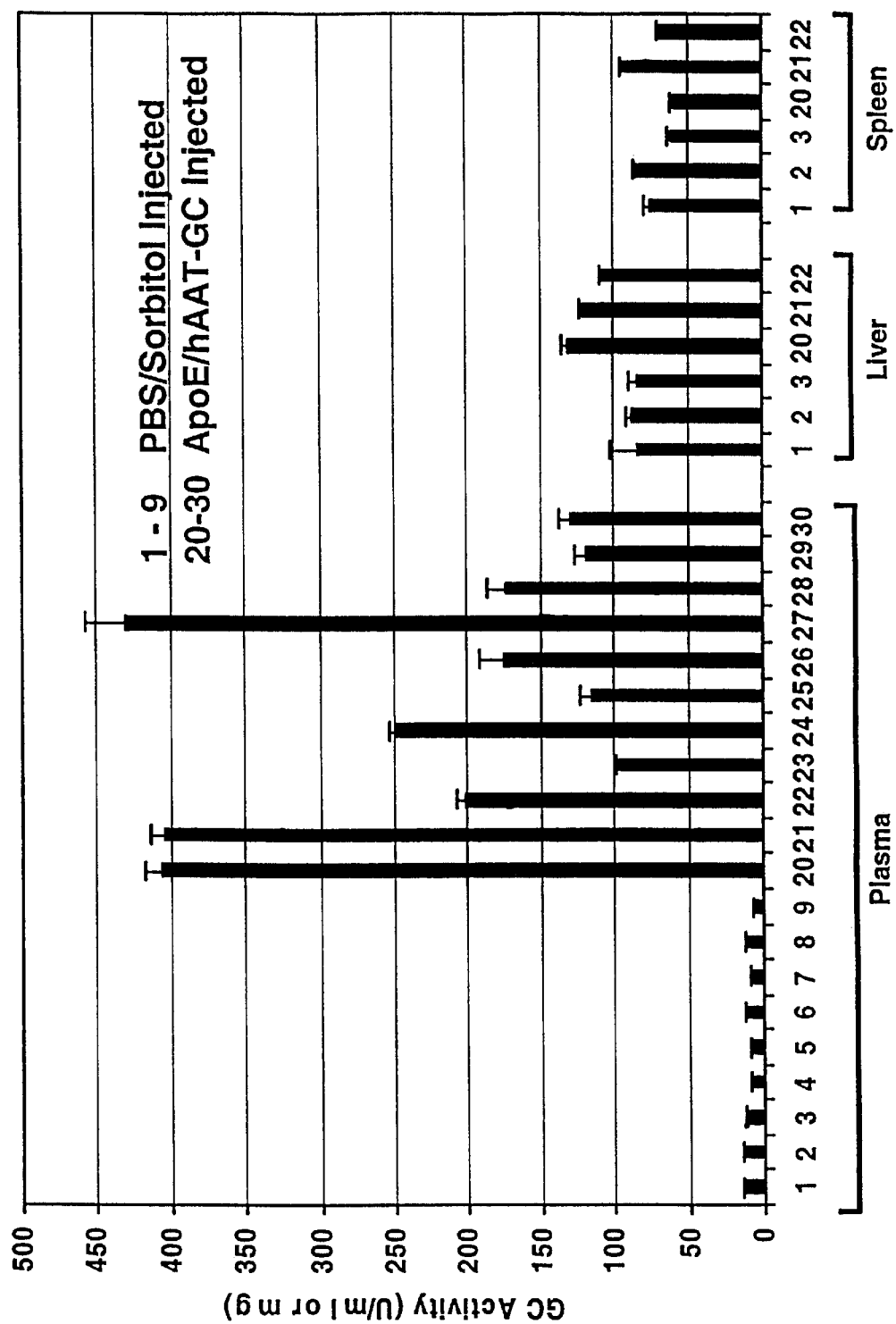
FIG. 11 shows GC expression in plasma, liver and spleen of portal vein injected Rag-1 mice. Four weeks after injection via portal vein, plasma, liver and spleen from either PBS/sorbitol injected mice (number 1–9) or AAV-ApoE/hAAT-hGC vector injected mice (number 20–30) were analyzed for GC activity.

The results from the four week time point are shown in FIG. 11. GC activity was detected in the plasma of all AAV-ApoEHCR/hAAT-hGC-injected animals at levels 7–30 fold higher than the pre-injected levels (data not shown) and the levels observed in the PBS injected control animals. Plasma GC activity ranged from 100–425 U/ml. GC activity was also observed in liver tissue of animals 4 weeks post-injection at levels approximately 1.5 times higher than in the PBS-injected animals. No significant changes in GC activity were observed in the spleen of these animals.

Figure 12:
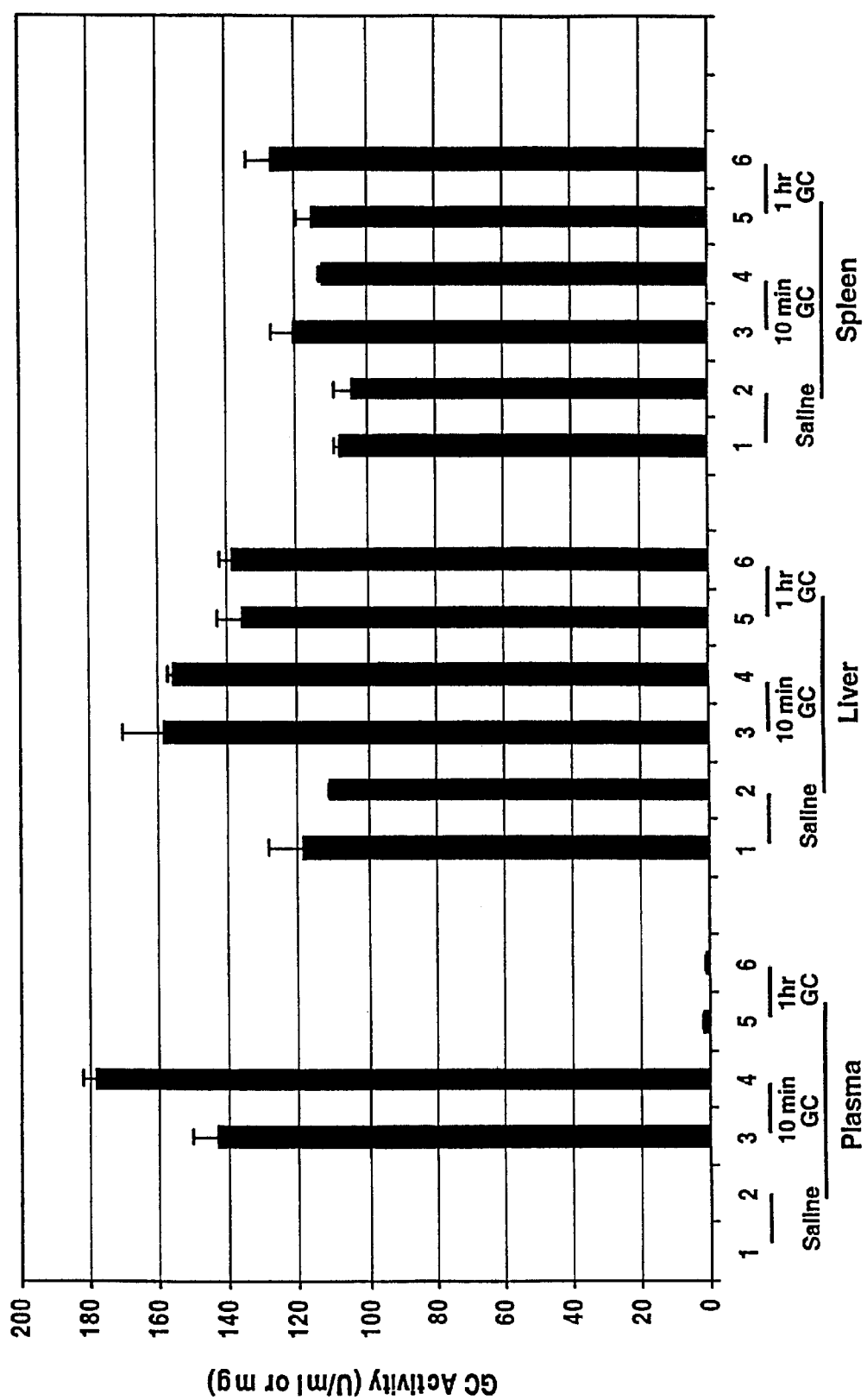
FIG. 12 shows GC activity in plasma, liver and spleen 10 or 60 minutes after tail vein injection of Cerezyme (60 IU/kg) or saline. Each group contained 2 mice.

Similar results were observed in animals injected with Cerezyme and sacrificed 10 min post injection (FIG. 12). The plasma levels increased to approximately 160 U/mil from barely detectable level in the control mice, and GC activity in liver tissue increased 1.4 fold. By 1 hour post-injection, Cerezyme was hardly detected in the plasma and had decreased slightly in the liver. No significant changes in GC activity were observed in the spleens of these animals compared to the PBS injected controls.

These data demonstrate that biologically active GC can be produced and secreted from the liver following delivery of AAV-ApoEHCR/hAAT-hGC to the bloodstream via the portal vein. The levels of GC observed in the liver 4 weeks post-injection were similar to the levels observed 10 minutes following administration of a therapeutic dose of Cerezyme.

These data, taken together, demonstrate the utility of AAV-mediated gene therapy for the treatment of Gaucher Disease.

---

We claim:

1. A method of delivering a recombinant adeno-associated virus (AAV) virion to a mammalian subject to treat a lysosomal storage disease, said method comprising:
    (a) providing a recombinant AAV virion composition which comprises AAV virions, wherein said AAV virions comprise a nucleic acid molecule, said nucleic acid molecule comprising a gene encoding a lysosomal storage enzyme missing or defective in the subject operably linked to control elements capable of directing the in vivo transcription and translation of said gene; and
    (b) delivering said recombinant AAV virion directly to the bloodstream of said subject, to result in expression of said gene for at least 13 weeks at a level which reduces lysosomal storage in said mammalian subject.

2. The method of claim 1, wherein the recombinant AAV virion is delivered intravenously.

3. The method of claim 2, wherein the recombinant AAV virion is delivered to the portal vein.

4. The method of claim 1, wherein the recombinant AAV virion is delivered intraarterially.

5. The method of claim 4, wherein the recombinant AAV virion is delivered to the hepatic artery.

6. The method of claim 1, wherein the gene is expressed in the liver of said subject.

7. The method of claim 1, wherein the lysosomal storage disease is MPS VII and the gene encodes β-glucuronidase.

8. The method of claim 1, wherein said recombinant AAV virion is delivered intravascularly.

* * * * *

UNITED STATES PATENT AND TRADEMARK OFFICE
CERTIFICATE OF CORRECTION

PATENT NO. : 6,582,692 B1
DATED : June 24, 2003
INVENTOR(S) : Podsakoff et al.

It is certified that error appears in the above-identified patent and that said Letters Patent is hereby corrected as shown below:

<u>Column 1,</u>
Line 3, please insert the following paragraph:
-- This invention was made with support under NIH Grant 5 R01 DK54285-04 from the National Institutes of Health, U.S. Department of Health and Human Services. Accordingly, the United States Government may have certain rights in this invention. --

Signed and Sealed this

Ninth Day of September, 2003

JAMES E. ROGAN
*Director of the United States Patent and Trademark Office*